(12) United States Patent
Johnson et al.

(10) Patent No.: US 11,903,713 B2
(45) Date of Patent: Feb. 20, 2024

(54) BIOFEEDBACK FOR AWARENESS AND MODULATION OF MENTAL STATE USING A NON-INVASIVE BRAIN INTERFACE SYSTEM AND METHOD

(71) Applicant: HI LLC, Los Angeles, CA (US)

(72) Inventors: Bryan Johnson, Los Angeles, CA (US); Husam Katnani, Braintree, MA (US); Jamu Alford, Lake Arrowhead, CA (US); Ricardo Jimenez-Martinez, Culver City, CA (US)

(73) Assignee: HI LLC, Los Angeles, CA (US)

( * ) Notice: Subject to any disclaimer, the term of this patent is extended or adjusted under 35 U.S.C. 154(b) by 462 days.

(21) Appl. No.: 17/177,975

(22) Filed: Feb. 17, 2021

(65) Prior Publication Data
US 2021/0251542 A1 Aug. 19, 2021

Related U.S. Application Data

(63) Continuation of application No. 16/364,338, filed on Mar. 26, 2019, now Pat. No. 11,006,876.
(Continued)

(51) Int. Cl.
*A61B 5/00* (2006.01)
*A61B 5/16* (2006.01)
*A61B 5/245* (2021.01)

(52) U.S. Cl.
CPC ............ *A61B 5/165* (2013.01); *A61B 5/0022* (2013.01); *A61B 5/0059* (2013.01); *A61B 5/245* (2021.01); *A61B 5/486* (2013.01); *A61B 5/6803* (2013.01); *A61B 5/742* (2013.01); *A61B 5/7405* (2013.01); *A61B 5/7455* (2013.01)

(58) Field of Classification Search
CPC ..... A61B 5/165; A61B 5/0022; A61B 5/0059; A61B 5/245; A61B 5/486; A61B 5/6803; A61B 5/7405; A61B 5/742; A61B 5/7455; A61B 5/24
See application file for complete search history.

(56) References Cited

U.S. PATENT DOCUMENTS 4,018,534 A 4/1977 Thorn et al.
4,207,892 A 6/1980 Binder
(Continued)

FOREIGN PATENT DOCUMENTS

EP 2294973 3/2011
EP 2939706 11/2015
(Continued)

OTHER PUBLICATIONS

Non-Final Office Action received in U.S. Appl. No. 16/856,524 dated Dec. 1, 2020.
(Continued)

*Primary Examiner* — Joel Lamprecht
(74) *Attorney, Agent, or Firm* — Michael J. Bolan; Vista IP Law Group, LLP

(57) ABSTRACT

A mental state awareness system comprises a non-invasive brain interface assembly configured for detecting brain activity of a user, a processor configured for determining a mental state of a user based on the detected brain activity, and a biofeedback device configured for automatically providing biofeedback to the user indicative of the determined mental state of the user.

11 Claims, 16 Drawing Sheets

Related U.S. Application Data

(60) Provisional application No. 62/818,786, filed on Mar. 15, 2019, provisional application No. 62/784,364, filed on Dec. 21, 2018.

(56) References Cited

U.S. PATENT DOCUMENTS

| | | | |
|---|---|---|---|
| 4,281,645 A | 8/1981 | Jobsis | |
| 4,515,165 A | 5/1985 | Carroll | |
| 4,655,225 A | 4/1987 | Dahne et al. | |
| 4,963,727 A | 10/1990 | Cova | |
| 5,090,415 A | 2/1992 | Yamashita | |
| 5,377,100 A | 12/1994 | Pope et al. | |
| 5,720,619 A | 2/1998 | Fisslinger | |
| 5,853,370 A | 12/1998 | Chance et al. | |
| 5,929,982 A | 7/1999 | Anderson | |
| 6,163,715 A | 12/2000 | Larsen et al. | |
| 6,240,309 B1 | 5/2001 | Yamashita et al. | |
| 6,384,663 B2 | 5/2002 | Cova et al. | |
| 6,488,617 B1 | 12/2002 | Katz | |
| 6,541,752 B2 | 4/2003 | Zappa et al. | |
| 6,683,294 B1 | 1/2004 | Herbert et al. | |
| 6,992,772 B2 | 1/2006 | Block | |
| 7,095,491 B2 | 8/2006 | Forstner et al. | |
| 7,356,365 B2 | 4/2008 | Schurman | |
| 7,507,596 B2 | 3/2009 | Yaung et al. | |
| 7,547,872 B2 | 6/2009 | Niclass et al. | |
| 7,613,504 B2 | 11/2009 | Rowe | |
| 7,667,400 B1 | 2/2010 | Goushcha | |
| 7,705,284 B2 | 4/2010 | Inoue et al. | |
| 7,714,292 B2 | 5/2010 | Agarwal et al. | |
| 7,774,047 B2 | 8/2010 | Yamashita et al. | |
| 7,899,506 B2 | 3/2011 | Xu et al. | |
| 8,026,471 B2 | 9/2011 | Itzler | |
| 8,078,250 B2 | 12/2011 | Chen et al. | |
| 8,082,015 B2 | 12/2011 | Yodh et al. | |
| 8,115,170 B2 | 2/2012 | Stellari et al. | |
| 8,168,934 B2 | 5/2012 | Niclass et al. | |
| 8,209,224 B2 | 6/2012 | Pradeep et al. | |
| 8,356,004 B2 | 1/2013 | Jung et al. | |
| 8,473,024 B2 | 6/2013 | Causevic et al. | |
| 8,609,162 B2 | 12/2013 | Giuliano et al. | |
| 8,633,431 B2 | 1/2014 | Kim | |
| 8,637,875 B2 | 1/2014 | Finkelstein et al. | |
| 8,754,378 B2 | 6/2014 | Prescher et al. | |
| 8,762,202 B2 | 6/2014 | Pradeep et al. | |
| 8,817,257 B2 | 8/2014 | Herve | |
| 9,012,860 B2 | 4/2015 | Nyman et al. | |
| 9,041,136 B2 | 5/2015 | Chia | |
| 9,058,081 B2 | 6/2015 | Baxter | |
| 9,076,707 B2 | 7/2015 | Harmon | |
| 9,101,279 B2 | 8/2015 | Ritchey et al. | |
| 9,114,140 B2 | 8/2015 | Giuliano et al. | |
| 9,131,861 B2 | 9/2015 | Ince et al. | |
| 9,160,949 B2 | 10/2015 | Zhang et al. | |
| 9,176,241 B2 | 11/2015 | Frach | |
| 9,178,100 B2 | 11/2015 | Webster et al. | |
| 9,190,552 B2 | 11/2015 | Brunel et al. | |
| 9,201,138 B2 | 12/2015 | Eisele et al. | |
| 9,209,320 B1 | 12/2015 | Webster | |
| 9,211,077 B2 | 12/2015 | Jung et al. | |
| 9,257,523 B2 | 2/2016 | Schneider et al. | |
| 9,257,589 B2 | 2/2016 | Niclass et al. | |
| 9,265,974 B2 | 2/2016 | You et al. | |
| 9,299,732 B2 | 3/2016 | Webster et al. | |
| 9,299,873 B2 | 3/2016 | Mazzillo et al. | |
| 9,312,401 B2 | 4/2016 | Webster | |
| 9,316,735 B2 | 4/2016 | Baxter | |
| 9,331,116 B2 | 5/2016 | Webster | |
| 9,339,227 B2 | 5/2016 | Darcy et al. | |
| 9,368,487 B1 | 6/2016 | Su et al. | |
| 9,401,448 B2 | 7/2016 | Bienfang et al. | |
| 9,407,796 B2 | 8/2016 | Dinten et al. | |
| 9,417,106 B2 | 8/2016 | Tobita | |
| 9,419,635 B2 | 8/2016 | Kumar et al. | |
| 9,431,439 B2 | 8/2016 | Soga et al. | |
| 9,440,064 B2 | 9/2016 | Wingeier et al. | |
| 9,442,201 B2 | 9/2016 | Schmand et al. | |
| 9,449,377 B2 | 9/2016 | Sarkar et al. | |
| 9,450,007 B1 | 9/2016 | Motta et al. | |
| 9,466,631 B2 | 10/2016 | Fallica et al. | |
| 9,476,979 B2 | 10/2016 | Drader et al. | |
| 9,478,579 B2 | 10/2016 | Dai et al. | |
| 9,495,684 B2 | 11/2016 | Jung et al. | |
| 9,529,079 B1 | 12/2016 | Droz | |
| 9,535,157 B2 | 1/2017 | Caley et al. | |
| 9,574,936 B2 | 2/2017 | Heinonen | |
| 9,625,580 B2 | 4/2017 | Kotelnikov et al. | |
| 9,627,569 B2 | 4/2017 | Harmon | |
| 9,639,063 B2 | 5/2017 | Dutton et al. | |
| 9,640,704 B2 | 5/2017 | Frey et al. | |
| 9,658,158 B2 | 5/2017 | Renna et al. | |
| 9,659,980 B2 | 5/2017 | McGarvey et al. | |
| 9,671,284 B1 | 6/2017 | Dandin | |
| 9,685,576 B2 | 6/2017 | Webster | |
| 9,702,758 B2 | 7/2017 | Nouri | |
| 9,704,205 B2 | 7/2017 | Akutagawa et al. | |
| 9,712,736 B2 | 7/2017 | Kearns et al. | |
| 9,728,659 B2 | 8/2017 | Hirigoyen et al. | |
| 9,729,252 B2 | 8/2017 | Tyler et al. | |
| 9,736,603 B2 | 8/2017 | Osborne et al. | |
| 9,741,879 B2 | 8/2017 | Frey et al. | |
| 9,753,351 B2 | 9/2017 | Eldada | |
| 9,767,246 B2 | 9/2017 | Dolinsky et al. | |
| 9,768,211 B2 | 9/2017 | Harmon | |
| 9,773,930 B2 | 9/2017 | Motta et al. | |
| 9,804,092 B2 | 10/2017 | Zeng et al. | |
| 9,812,438 B2 | 11/2017 | Schneider et al. | |
| 9,831,283 B2 | 11/2017 | Shepard et al. | |
| 9,851,302 B2 | 12/2017 | Mattioli Della Rocca et al. | |
| 9,867,250 B1 | 1/2018 | Powers et al. | |
| 9,869,753 B2 | 1/2018 | Eldada | |
| 9,881,963 B1 | 1/2018 | Chen et al. | |
| 9,882,003 B1 | 1/2018 | Aharoni | |
| 9,886,095 B2 | 2/2018 | Pothier | |
| 9,899,544 B1 | 2/2018 | Mazzillo et al. | |
| 9,899,557 B2 | 2/2018 | Muscara' et al. | |
| 9,939,316 B2 | 4/2018 | Scott et al. | |
| 9,939,536 B2 | 4/2018 | O'Neill et al. | |
| 9,943,698 B2 | 4/2018 | Chase et al. | |
| 9,946,344 B2 | 4/2018 | Ayaz et al. | |
| D817,553 S | 5/2018 | Aaskov et al. | |
| 10,016,137 B1 | 7/2018 | Yang et al. | |
| D825,112 S | 8/2018 | Saez | |
| 10,056,415 B2 | 8/2018 | Na et al. | |
| 10,091,554 B1 | 10/2018 | Newell et al. | |
| 10,141,458 B2 | 11/2018 | Zhang et al. | |
| 10,143,414 B2 | 12/2018 | el Kaliouby et al. | |
| 10,157,954 B2 | 12/2018 | Na et al. | |
| 10,158,038 B1 | 12/2018 | Do Valle et al. | |
| 10,188,860 B2 | 1/2019 | Wingeier et al. | |
| 10,219,700 B1 | 3/2019 | Yang et al. | |
| 10,234,942 B2 | 3/2019 | Connor | |
| 10,256,264 B2 | 4/2019 | Na et al. | |
| 10,258,760 B1 | 4/2019 | Sherpa et al. | |
| 10,340,408 B1 | 7/2019 | Katnani | |
| 10,515,993 B2 | 12/2019 | Field et al. | |
| 10,517,521 B2 | 12/2019 | Kallouby et al. | |
| 10,546,233 B1 | 1/2020 | Bhattacharyya et al. | |
| 10,579,925 B2 | 1/2020 | Kasabov et al. | |
| 10,558,171 B2 | 2/2020 | Kondo | |
| 10,586,454 B2 | 3/2020 | Toyoda et al. | |
| 10,593,349 B2 | 3/2020 | Park | |
| 10,600,179 B2 | 3/2020 | Mcvey | |
| 10,628,741 B2 | 4/2020 | el Kaliouby et al. | |
| 10,636,318 B2 | 4/2020 | Letterese et al. | |
| 11,006,876 B2 * | 5/2021 | Johnson | A61B 5/742 |
| 2003/0176806 A1 | 9/2003 | Pineda et al. | |
| 2004/0049134 A1 | 3/2004 | Tosaya et al. | |
| 2005/0061986 A1 | 3/2005 | Kardynal et al. | |
| 2006/0150989 A1 | 7/2006 | Migaly | |
| 2006/0161218 A1 | 7/2006 | Danilov | |
| 2008/0177197 A1 | 7/2008 | Lee et al. | |
| 2009/0012402 A1 | 1/2009 | Mintz | |

(56) References Cited

U.S. PATENT DOCUMENTS

| | | |
|---|---|---|
| 2009/0083129 A1 | 3/2009 | Pradeep et al. |
| 2011/0208675 A1 | 8/2011 | Shoureshi et al. |
| 2012/0029304 A1 | 2/2012 | Medina et al. |
| 2012/0172743 A1 | 7/2012 | Aguilar et al. |
| 2013/0032713 A1 | 2/2013 | Barbi et al. |
| 2013/0221221 A1 | 8/2013 | Bouzid et al. |
| 2013/0289385 A1 | 10/2013 | Lozano et al. |
| 2013/0297599 A1 | 11/2013 | Henshall |
| 2013/0311132 A1 | 11/2013 | Tobita |
| 2013/0342835 A1 | 12/2013 | Blacksberg |
| 2014/0023999 A1 | 1/2014 | Greder |
| 2014/0027607 A1 | 1/2014 | Mordarski et al. |
| 2014/0021119 A1 | 7/2014 | Pacala et al. |
| 2014/0191115 A1 | 7/2014 | Webster et al. |
| 2014/0200432 A1* | 7/2014 | Banerji ............... G16H 20/30 607/54 |
| 2014/0228701 A1 | 8/2014 | Chizeck et al. |
| 2014/0275891 A1 | 9/2014 | Muehlemann et al. |
| 2014/0291481 A1 | 10/2014 | Zhang et al. |
| 2014/0303450 A1 | 10/2014 | Caponi |
| 2015/0041625 A1 | 2/2015 | Dutton |
| 2015/0041627 A1 | 2/2015 | Webster |
| 2015/0054111 A1 | 2/2015 | Niclass et al. |
| 2015/0077279 A1 | 3/2015 | Song |
| 2015/0150505 A1 | 6/2015 | Kaskoun et al. |
| 2015/0192677 A1 | 7/2015 | Yu et al. |
| 2015/0200222 A1 | 7/2015 | Webster |
| 2015/0248651 A1 | 9/2015 | Akutagawa et al. |
| 2015/0290454 A1 | 10/2015 | Tyler et al. |
| 2015/0293224 A1 | 10/2015 | Eldada et al. |
| 2015/0297109 A1 | 10/2015 | Garten |
| 2015/0327777 A1 | 11/2015 | Kostic et al. |
| 2015/0333095 A1 | 11/2015 | Fallica et al. |
| 2015/0338917 A1 | 11/2015 | Steiner et al. |
| 2015/0355462 A1 | 12/2015 | Saito et al. |
| 2015/0364635 A1 | 12/2015 | Bodlovic et al. |
| 2016/0049765 A1 | 2/2016 | Eldada |
| 2016/0099371 A1 | 4/2016 | Webster |
| 2016/0119983 A1 | 4/2016 | Moore |
| 2016/0150963 A1 | 6/2016 | Roukes et al. |
| 2016/0161600 A1 | 6/2016 | Eldada et al. |
| 2016/0181302 A1 | 6/2016 | McGarvey et al. |
| 2016/0218236 A1 | 7/2016 | Dhulla et al. |
| 2016/0220163 A1 | 8/2016 | Yamada |
| 2016/0242690 A1 | 8/2016 | Principe et al. |
| 2016/0270656 A1 | 9/2016 | Samec et al. |
| 2016/0278715 A1 | 9/2016 | Yu et al. |
| 2016/0287107 A1 | 10/2016 | Szabados |
| 2016/0341656 A1 | 11/2016 | Liu et al. |
| 2016/0356718 A1 | 12/2016 | Yoon et al. |
| 2016/0357260 A1 | 12/2016 | Raynor et al. |
| 2017/0030769 A1 | 2/2017 | Clemens et al. |
| 2017/0042439 A1 | 2/2017 | Yeow |
| 2017/0047372 A1 | 2/2017 | McGarvey et al. |
| 2017/0052065 A1 | 2/2017 | Sharma et al. |
| 2017/0118423 A1 | 4/2017 | Zhou et al. |
| 2017/0131143 A1 | 5/2017 | Andreou et al. |
| 2017/0139041 A1 | 5/2017 | Drader et al. |
| 2017/0141100 A1 | 5/2017 | Tseng et al. |
| 2017/0176579 A1 | 6/2017 | Niclass et al. |
| 2017/0176596 A1 | 6/2017 | Shpunt et al. |
| 2017/0179173 A1 | 6/2017 | Mandai et al. |
| 2017/0186798 A1 | 6/2017 | Yang et al. |
| 2017/0188876 A1 | 7/2017 | Marci et al. |
| 2017/0202518 A1 | 7/2017 | Furman et al. |
| 2017/0229037 A1 | 8/2017 | Gazzaley |
| 2017/0262943 A1 | 9/2017 | Akutagawa et al. |
| 2017/0265822 A1 | 9/2017 | Du |
| 2017/0276545 A1 | 9/2017 | Henriksson |
| 2017/0299700 A1 | 10/2017 | Pacala et al. |
| 2017/0303789 A1 | 10/2017 | Tichauer et al. |
| 2017/0314989 A1 | 11/2017 | Mazzillo et al. |
| 2017/0352283 A1 | 12/2017 | Lau |
| 2017/0363467 A1 | 12/2017 | Clemens et al. |
| 2018/0003821 A1 | 1/2018 | Imai |
| 2018/0014741 A1 | 1/2018 | Chou |
| 2018/0019268 A1 | 1/2018 | Zhang et al. |
| 2018/0026147 A1 | 1/2018 | Zhang et al. |
| 2018/0027196 A1 | 1/2018 | Yang et al. |
| 2018/0033895 A1 | 2/2018 | Mazzillo et al. |
| 2018/0039053 A1 | 2/2018 | Kremer et al. |
| 2018/0045816 A1 | 2/2018 | Jarosinski et al. |
| 2018/0062345 A1 | 3/2018 | Bills et al. |
| 2018/0069043 A1 | 3/2018 | Pan et al. |
| 2018/0081061 A1 | 3/2018 | Mandai et al. |
| 2018/0089848 A1 | 3/2018 | Yang et al. |
| 2018/0090526 A1 | 3/2018 | Mandai et al. |
| 2018/0090536 A1 | 3/2018 | Mandai et al. |
| 2018/0092557 A1* | 4/2018 | Bickford ............... A61B 5/375 |
| 2018/0102442 A1 | 4/2018 | Wang et al. |
| 2018/0103528 A1 | 4/2018 | Moore |
| 2018/0167606 A1 | 6/2018 | Cazaux et al. |
| 2018/0175230 A1 | 6/2018 | Droz et al. |
| 2018/0189678 A1 | 7/2018 | Gupta et al. |
| 2018/0217261 A1 | 8/2018 | Wang |
| 2018/0278984 A1 | 9/2018 | Aimone |
| 2018/0366342 A1 | 12/2018 | Inoue et al. |
| 2019/0006399 A1 | 1/2019 | Otake et al. |
| 2019/0021657 A1 | 1/2019 | Mohammadrezazadeh et al. |
| 2019/0082990 A1* | 3/2019 | Poltorak ............... A61B 5/377 |
| 2019/0088697 A1 | 3/2019 | Furukawa et al. |
| 2019/0090526 A1 | 3/2019 | Alshatwi et al. |
| 2019/0113385 A1 | 4/2019 | Fukuchi |
| 2019/0175068 A1 | 6/2019 | Everdell |
| 2019/0200888 A1 | 7/2019 | Poltorak |
| 2019/0201691 A1 | 7/2019 | Poltorak |
| 2019/0224441 A1 | 7/2019 | Poltorak |
| 2019/0246929 A1 | 8/2019 | Poltorak |
| 2019/0247662 A1 | 8/2019 | Poltorak |
| 2019/0321583 A1 | 10/2019 | Poltorak |
| 2019/0355773 A1 | 11/2019 | Field et al. |
| 2019/0378869 A1 | 12/2019 | Field et al. |
| 2021/0378570 A1* | 12/2021 | Laine .................... A61B 5/246 |

FOREIGN PATENT DOCUMENTS

| | | |
|---|---|---|
| WO | 8804034 | 6/1988 |
| WO | WO02043564 | 6/2002 |
| WO | 2008144831 | 12/2008 |
| WO | 2012135068 | 10/2012 |
| WO | WO2012135068 | 10/2012 |
| WO | 2013034770 | 3/2013 |
| WO | 2013066959 | 5/2013 |
| WO | WO2014055932 | 4/2014 |
| WO | 2015052523 | 4/2015 |
| WO | 2016166002 | 10/2016 |
| WO | 2017004663 | 1/2017 |
| WO | 2017130682 | 8/2017 |
| WO | 2017150146 | 9/2017 |
| WO | 2017203936 | 11/2017 |
| WO | 2018007829 | 1/2018 |
| WO | 2018033751 | 2/2018 |
| WO | 2018122560 | 7/2018 |

OTHER PUBLICATIONS

Response filed in U.S. Appl. No. 16/856,524, filed Feb. 11, 2021.

Notice of Allowance received in U.S. Appl. No. 16/856,524 dated Feb. 26, 2021.

PCT International Search Report and Written Opinion for International Appln. No. PCT/US2020/025971, Applicant HI LLC, forms PCT/ISA/210, 220 and 237 dated Sep. 15, 2020 (15 pages).

Judith Amores, et al., "Promoting Relaxation Using Virtual Reality, Olfactory Interfaces and Wearable EEG," 2018 IEEE 15th International Conference on Waerable and Implantable Body Sensor Networks; Mar. 4, 2018, (4 pages).

PCT International Search Report and Written Opinion for International Appln. No. PCT/US2020/029031, Applicant HI LLC, forms PCT/ISA/210, 220 and 237 dated Sep. 2, 2020 (18 pages).

M. Teplan, "Fundamentals of EEG Measurement", Measurement Science Review, vol. 2, Section 2, 2002; 11 pages.

(56) References Cited

OTHER PUBLICATIONS

Samat Moldakarimova, et al., "Perceptual priming leads to reduction of gamma frequency oscillations", PNAS, Mar. 23, 2010, vol. 107, No. 12; 6 pages.

Peter Lintelle, Sensory Marketing Aspects: Priming, Expectations, Crossmodal Correspondences & More; CreateSpace Independent Publishing Platform, Jul. 23, 2014, ISBN-10: 1500616400, ISBN-13: 978-1500616403; 3 pages.

Yang Jiang, et al., "Turning Up the Old Brain with New Tricks: Attention Training via Neurofeedback", Frontiers in Aging Neuroscience; Mar. 2017; vol. 9; Article 52; 9 pages.

John D. E. Gabrieli, et al., "The role of left prefrontal cortex in language and memory", Proc. Natl. Acad. Sci. USA, vol. 95, pp. 906-913, Feb. 1998; 8 pages.

Stanislas Dehaene, et al., "Imaging unconscious semantic priming", Nature; vol. 395; Oct. 8, 1998; 4 pages.

Elena Boto, et al., "A new generation of magnetoencephalography: Room temperature measurements using optically-pumped magnetometers", NeuroImage 149 (2017) 404-414; 11 pages.

Fernando Lopes da Silva, "EEG and MEG: Relevance to Neuroscience", Center of Neuroscience; http://dx.doi.org/10.1016/j.neuron.2013.10.017; 17 pages.

Patrick Gomez, et al., "Relationships Between Musical Structure and Psychophysiological Measures of Emotion", American Psychological Association, vol. 7, No. 2, 2007, pp. 377-387, 10 pages.

Stefan K. Ehrlich, et al., "A closed-loop, music-based brain-computer interface for emotion mediation," PLoS ONE 14(3): e0213516. https://doi.org/10.1371/journal.pone.0213516; Mar. 18, 2019.

PCT International Search Report and Written Opinion for International Appln. No. PCT/US2019/024027, Applicant HI LLC, forms PCT/ISA/210, 220 and 237 dated Aug. 19, 2019 (13 pages).

Lee, B.T., Seok, J.H., Lee., B.C, Cho, S.W., Chai, J.H., Chol, I.G., Ham, B.J., "Neural correlates of affective processing in response to sad and angry facial stimuli in patients with major depressive disorder," Prog Neuropsychopharmacol Biol Psychiatry, 32(3), 778-85 (2008.

A.C. Felix-Ortiz, A.C., Burgos-Robles, A., Bhagat, N.D., Leppla, C.A., Tye, K.M., "Bidirectional modulation of anxiety-related and social behaviors by amygdala projections to the medial prefrontal cortex," Neuroscience 321, 197-209 (2016).

Beauregard, M., Levesque, J. & Bourgouin, P., "Neural correlates of conscious self-regulation of emotion," J. Neurosci. (2001): 21, RC165.

Phan, K. L., Wager, T., Taylor, S. F. & Liberzon, I., "Functional neuroanatomy of emotion: a meta-analysis of emotion activation studies in PET and fMRI," Neuroimage, 16, 331-348 (2002).

Canli, T. & Amin, Z., "Neuroimaging of emotion and personality: scientific evidence and ethical considerations," Brain Cogn., 50, 414-431 (2002).

McCloskey, M. S., Phan, K. L. & Coccaro, E. F., "Neuroimaging and personality disorders," Curr. Psychiatry Rep., 7, 65-72 (2005).

Heekeren, H. R., Marrett, S., Bandettini, P. A. & Ungerleider, L. G., "A general mechanism for perceptual decision-making in the human brain," Nature, 431, 859-862 (2004).

Shin LM, Rauch SL, Pitman RK., "Amygdala, Medial Prefrontal Cortex, and Hippocampal Function in PTSD," Ann N Y Acad Sci., 1071(1) (2006).

Lis E, Greenfield B, Henry M, Guile JM, Dougherty G., "Neuroimaging and genetics of borderline personality disorder: a review," J Psychiatry Neurosci., 32(3), 162-173 (2007).

Etkin A, Wager TD, "Functional neuroimaging of anxiety: a meta-analysis of emotional processing in PTSD, social anxiety disorder, and specific phobia," Am J Psychiatry, 164(10), 1476-1488 (2007).

Hamilton, P., Etkin A., "Functional Neuroimaging of Major Depressive Disorder: A Meta-Analysis and New Integration of Baseline Activation and Neural Response Data", Am J Psychiatry, 169(7), 693-703 (2012).

Sheline YI, Price JL, Yan Z, Mintun MA, "Resting-state functional MRI in depression unmasks increased connectivity between networks via the dorsal nexus," Proc Natl Acad Sci., 107(24), 11020-11025 (2010).

Bari A, Robbins TW, "Inhibition and impulsivity: Behavioral and neural basis of response control," Prog Neurobiol., 108:44-79 (2013).

Kagias, Konstantinos et al. "Neuronal responses to physiological stress," Frontiers in genetics, 3:222 (2012).

Clark, Ian A., et al., "First steps in using machine learning on fMRI data to predict intrusive memories of traumatic film footage", 0005-7967/ 2014 The Authors. Published by Elsevier Ltd. Behaviour Research and Therapy. This is an open access article under the CC BY license (http://creativecommons.org/licenses/by/3.0/); 10 pgs.

George, Mark S., M.D., "Changes in Mood and Hormone Levels After Rapid-Rate Transcranial Magnetic Stimulation (rTMS) of the Prefrontal Cortex", Journal of Neuropsychiatry, vol. 8, No. 2, Spring 1996, 9 pages.

Milad, M. R., et al., "Neuroscience of fear extinction: Implications for assessment and treatment of fear-based and anxiety related disorders", Behaviour Research and Therapy (2014), http://dx.doi.org/10.1016/j.brat.2014.08.006, 7 pages.

S.Z.K, Tan et al., "Eternal sunshine of the neuromodulated mind: Altering fear memories through neuromodulation", Experimental Neurology 314 (2019) 9-19, 11 pages.

Zhang, Fei-Fei, et al., "Brain structure alterations in depression: Psychoradiological evidence", CNS Neurosci T 2018, John Wiley & Sons Ltd her. 2018;24:994-1003, 10 pages.

Tim M. Tierney, et al., "Cognitive neuroscience using wearable magnetometer arrays: Non-invasive assessment of language function," NeuroImage 181 (2018) pp. 513-520.

Pour, et al., "Brain-Computer Interface: Next Generation Thought Controlled Distributed Video Game Development Platform," IEEE, 7 pages, May 8, 2008.

Pineda et al., "The functional significance of mu rhythms: Translating "seeing" and "hearing" into "doing"," Brain Research Reviews 50, pp. 57-68, 2005.

Pineda et al., "Learning to Control Brain Rhythms: Making A Brain-Computer Interface Possible," IEEE Trans Neural Sys Rehab, Jul. 15, 2002.

S. G. Mason, "A Brain-Controlled Switch for Asynchronous Control Applications," IEE Transactions on Biomedical Engineering, vol. 47, No. 10, Oct. 2000.

International Search Report and Written Opinion received in International Application No. PCT/US20/028820, dated Aug. 26, 2020.

International Search Report and Written Opinion received in International Application No. PCT/US20/027537, dated Sep. 7, 2020.

International Search Report and Written Opinion received in International Application No. PCT/US20/034062, dated Aug. 26, 2020.

Blutman, et al., "A 0.1 pJ Freeze Vernier Time-to-Digital Converter in 65nm CMOS," 2014 International Symposium on Circuits and Systems (ISCAS), Melbourne, Australia.

De Heyn, et al., "A Fast Start-up 3GHz-10GHz Digitally Controlled Oscillator for UWB Impulse Radio in 90nm CMOS," 2007 European Solid-State Circuits Conference—(ESSCIRC), Munich, Germany, pp. 484-487.

Henderson, et al., "A 256×256 40nm/90nm CMOS 3D-Stacked 120dB-Dynamic-Range Reconfigurable Time-Resolved SPAD Imager," 2019 IEEE International Solid-State Circuits Conference—(ISSCC), San Francisco, CA, USA, 2019, pp. 106-108. doi: 10.1109/ISSCC.2019.8662355.

Henderson, et al., A 192×128 Time Correlated SPAD Image Sensor in 40-nm CMOS Technology IEEE Journal of Solid-State Circuits, 2019.

Mita, et al., "High-Speed and Compact Quenching Circuit for Single-Photon Avalanche Diodes," IEEE Transactions on Instrumentation and Measurement, vol. 57, No. 3, Mar. 2008. pp. 543-547.

Richardson, et al., "A 32×32 50ps Resolution 10 bit Time to Digital Converter Array in 130nm CMOS for Time Correlated Imaging," CICC 2009 Proceedings of the IEEE 2009 Custom Integrated Circuits Conference, IEEE Society, San Jose, U.S.A., pp. 77-80, Sep. 13, 2009. https://doi.org/doi:10.1109/CICC.2009.5280890.

(56) References Cited

OTHER PUBLICATIONS

International Search Report and Written Opinion received in International Application No. PCT/US2018/058580 dated Feb. 12, 2019.
International Search Report and Written Opinion received in International Application No. PCT/US2018/062777 dated Feb. 13, 2019.
Bellis, Stephen et al., Photon counting imaging: the DigitalAPD, Society of Photo-Optical Instrumentation Engineers (SPIE) Conference Series, Feb. 2006, vol. 6068, pp. 111-120.
Cambie, Dario et al., Every photon counts: understanding and optimizing photon paths in luminescent solar concentrator-based photomicroreactors (LSC-PMs), React. Chem. Eng., Feb. 2017, 561-566.
Dalla Mora, et al., Fast-Gated Single-Photon Avalanche Diode for Wide Dynamic Range Near Infrared Spectroscopy, IEEE Journal of Selected Topics in Quantum Electronics, vol. 16, No. 4, Jul./Aug. 2010, 1023-1030.
Dalla Mora, et al., Memory effect in silicon time-gated single-photon avalanche diodes, Journal of Applied Physics 117, 114501 (2015).
Dalla Mora, et al., Memory effect in silicon time-gated single-photon avalanche diodes, http://dx.doi.org/10.1063/1.4915332, Journal of Applied Physics 117, 114501, 2015 ,Jan. 7, 2015.
Dutton, et al., A Time-Correlated Single-Photon-Counting Sensor with 14GS/s Histogramming Time-to-Digital Converter, 2015 IEEE International Solid-State Circuits Conference ISSCC 2015 / SESSION 11 / Sensors and Imagers for Life Sciences / 11.5.
Fisher, et al., A Reconfigurable Single-Photon-Counting Integrating Receiver for Optical Communications, IEEE Journal of Solid-State Circuits, vol. 48, No. 7, Jul. 2013, https://www.researchgate.net/publication/260626902.
Gallivanoni, et al., Progress in Quenching Circuits for Single Photon Avalanche Diodes, IEEE Transactions on Nuclear Science, vol. 57, No. 6, Dec. 2010.
Gnecchi, et al., A 1×16 SiPM Array for Automotive 3D Imaging LiDAR Systems.
Harmon, Eric S. et al., Compound Semiconductor SPAD Arrays, LightSpin Technologies, http://www.lightspintech.com/publications.html.
Lee, et al., High-Performance Back-Illuminated Three-Dimensional Stacked Single-Photon Avalanche Diode Implemented in 45-nm CMOS Technology, IEEE Journal of Selected Topics in Quantum Electronics 6, 1-9 (2018).
Mandai, et al., A 4×4×416 digital SiPM array with 192 TDCs for multiple high-resolution timestamp acquisition, 2013 JINST 8 P05024.
Maruyama, et al., A 1024×8, 700-ps Time-Gated SPAD Line Sensor for Planetary Surface Exploration With Laser Raman Spectroscopy and LIBS, IEEE Journal of Solid-State Circuits, vol. 49, No. 1, Jan. 2014 ,2014 ,179-189.
Mora, Alberto D. et al., Fast-Gated Single-Photon Avalanche Diode for Wide Dynamic Range Near Infrared Spectroscopy, IEEE Journal of Selected Topics in Quantum Electronics, vol. 16, No. 4, pp. 1023-1030, Jul./Aug. 2010.
Parmesan, et al., A 256×256 SPAD array with in-pixel Time to Amplitude Conversion for Fluorescence Lifetime Imaging Microscopy, 2015.
Puszka, et al., Time-resolved diffuse optical tomography using fast-gated single-photon avalanche diodes, Biomedical optics express, 2013, vol. 4, No. 8, pp. 1351-1365 (Year: 2013).
Takai, et al., Single-Photon Avalanche Diode with Enhanced NIR-Sensitivity for Automotive LIDAR Systems, Sensors, 2016, 16(4): 459, pp. 1-9 (Year: 2016).
Zhang, et al., A CMOS SPAD Imager with Collision Detection and 128 Dynamically Reallocating TDCs for Single-Photon Counting and 3D Time-of-Flight Imaging, Sensors (Basel, Switzerland), 18(11), 4016. doi:10.3390/s18114016.

\* cited by examiner

BIOFEEDBACK FOR AWARENESS AND MODULATION OF MENTAL STATE USING A NON-INVASIVE BRAIN INTERFACE SYSTEM AND METHOD

RELATED APPLICATION DATA

The present application is a continuation of U.S. patent application Ser. No. 16/364,338, filed Mar. 26, 2019 (now U.S. Pat. No. 11,006,876), which claims the benefit of U.S. Provisional Patent Application 62/784,364, filed Dec. 21, 2018, and U.S. Provisional Patent Application 62/818,786, filed Mar. 15, 2019, which are expressly incorporated herein by reference.

FIELD OF THE INVENTION

The present inventions relate to methods and systems for non-invasive measurements in the human body, and in particular, methods and systems related to detecting a mental state of a human and providing biofeedback of that mental state.

BACKGROUND OF THE INVENTION

It is generally known that awareness of one's subconscious mental state, such as anxiety, focus, attention, creativity, positive or negative reflections/attitude on experiences or the use of objects, the employment of certain critical cognitive brain areas, etc., may lead to better emotional mood regulation and more objective decision-making. However, the conscious mind typically has peripheral or no awareness of subconscious mental states. Thus, if a person has a negative or unhealthy mental state (e.g., anxiety) within the context of a life or work experience, such person may not be aware of such mental state, and therefore, will be unable to take corrective actions (e.g., modifying or creating a new life or work experience) in order to alleviate or change this mental state.

There remains a need to make a person consciously aware of his or her subconscious mental state in a normal life and work environment, so that such human may better regulate his or her emotions or make more objective decisions.

SUMMARY OF THE INVENTION

In accordance with a first aspect of the present inventions, a mental state awareness system comprises a non-invasive brain interface assembly (e.g., an optical measurement assembly, magnetic measurement assembly, etc.) configured for detecting brain activity from a brain of a user. The non-invasive brain interface assembly may comprise, e.g., at least one detector configured for detecting energy (e.g., optical energy or magnetic energy) from the brain of the user, and processing circuitry configured for identifying the brain activity in response to detecting the energy from the brain of the user. In one embodiment, the non-invasive brain interface assembly comprises a head-worn unit carrying the energy source(s), and an auxiliary non-head-worn unit carrying the processing circuitry.

The mental state awareness system further comprises a processor configured for determining a mental state of a user (e.g., anxiety, focus, attention, creativity, positive or negative reflections/attitude on experiences or the use of objects, and the employment of certain critical cognitive brain areas) based on the detected brain activity.

The mental state awareness system further comprises a biofeedback device configured for automatically providing biofeedback to the user indicative of the determined mental state of the user. In one embodiment, the biofeedback device is configured for providing/directing vibrational signals (e.g., encoded with one or more messages) to the user indicative of the determined mental state of the user through peripheral somatosensation. In another embodiment, the biofeedback device is configured for providing/directing audio or visual signals to the user indicative of the determined mental state of the user.

The mental state awareness system optionally comprises a peripheral device configured for providing additional life/work context to the user. In one embodiment, the peripheral device is configured for being programmed with one of a plurality of user experiences corresponding to the additional life/work context. In another embodiment, the peripheral device is configured for automatically providing the additional life/work context to the user in response to the determined mental state of the user, such that the mental state of the user is modified. The mental state awareness system optionally comprises a database, sever, or cloud structure configured for tracking a brain activity history of the user. In this case, the processor may be configured for determining the mental state of the user further based on the tracked brain activity history of the user. The processor may be configured for determining the mental state of the user further based on tracked brain activity of a pool of users and/or tracking life/work context of the user, and acquiring meta data in depth assessment of awareness and behavior modulation patterns of the user.

In accordance with a second aspect of the present inventions, a method of making user aware of a mental state comprises detecting (e.g., optically detected, magnetically detected, etc.) brain activity from a brain of a user using a non-invasive brain interface. One method further comprises detecting energy from the brain of the user, and identifying the brain activity in response to detecting the energy from the brain of the user.

The method further comprises determining a mental state of a user (one of anxiety, focus, attention, creativity, positive or negative reflections/attitude on experiences or the use of objects, and the employment of certain critical cognitive brain areas) based on the detected brain activity.

The method further comprises automatically providing biofeedback to the user indicative of the determined mental state of the user. In one method, providing biofeedback to the user comprises providing/directing vibrational signals (e.g., encoded with one or more messages) to the user indicative of the determined mental state of the user through peripheral somatosensation. In another method, providing biofeedback to the user comprises providing/directing audio or visual signals to the user indicative of the determined mental state of the user.

The method optionally comprises providing additional life/work context to the user via a peripheral device. The additional life/work context may be provided to the user in response to the determined mental state of the user, such that the mental state of the user is modified. The method may further comprise programming the peripheral device with one of a plurality of user experiences corresponding to the additional life/work context.

The method optionally comprises tracking a brain activity history of the user. In this case, the mental state of the user is may be determined further based on the tracked brain activity history of the user.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
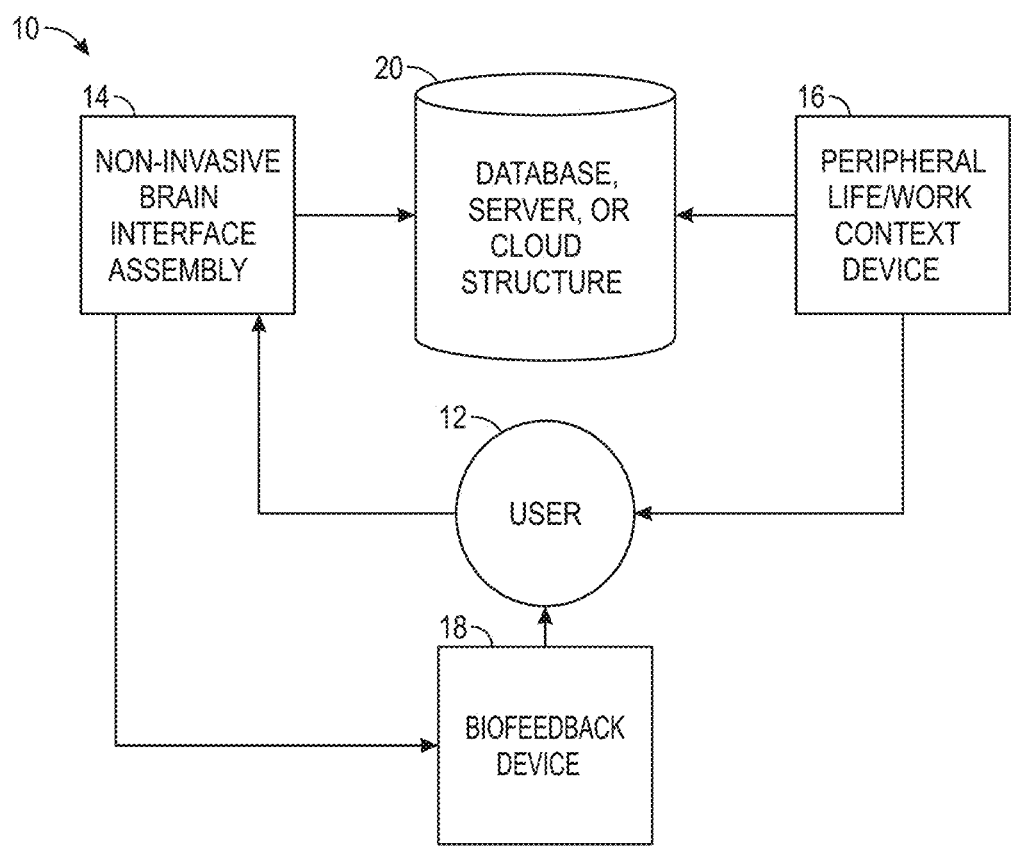
FIG. 1 is a block diagram of a non-invasive mental state awareness system constructed in accordance with one embodiment of the present inventions.
Figure 2:
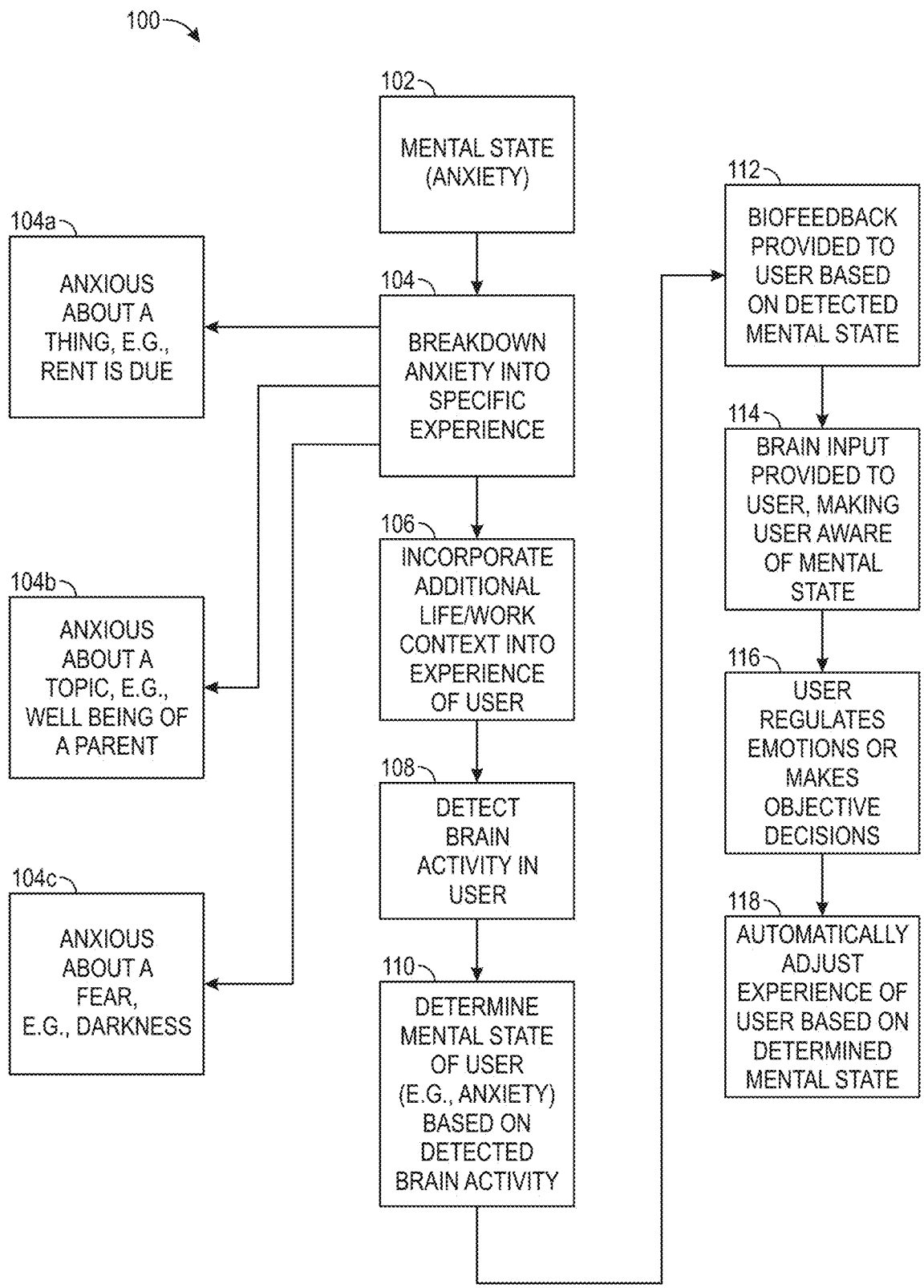
FIG. 2 is a flow diagram illustrating one method of operating the mental state awareness systems described herein.

Referring now to FIG. 1, a generalized embodiment of a non-invasive mental state awareness system 10 constructed in accordance with the present inventions will be described. The non-invasive mental state awareness system 10 advantageously closes the loop between brain interfaces and self-awareness and behavior modulation.

The mental state awareness system 10 comprises a non-invasive brain interface assembly 14 configured for detecting brain activity of a user 12. As will be discussed in further detail below, the brain interface assembly 14 can be optically-based, magnetically-based, or based on any other modality that enables it to non-invasively detect brain activity of the user 12 (i.e., through the intact skin and skull of the user 12), through the use of sensitive electronics, as will be described below, and is designed to be worn by the user 12. As will also be discussed in further detail below, the non-invasive brain interface assembly 14 is portable in that it can be worn by the user 12. The brain interface assembly 14 is also configured for determining a mental state (such as, e.g., anxiety, focus, attention, creativity, positive or negative reflections/attitude on experiences or the use of objects, the employment of certain critical cognitive brain areas, etc.) of the user 12 based on the detected brain activity, although this function can be performed by other processing components in the mental state awareness system 10, as described in further detail below.

The mental state of the user 12 may be determined based on the detected brain activity in any one of a variety of manners. In one embodiment, a univariate approach in determining the mental state of the user 12 may be performed, i.e., the brain activity can be detected in a plurality (e.g., thousands) of separable cortical modules of the user 12, and the brain activity obtained from each cortical module can be analyzed separately and independently. In another embodiment, a multivariate approach in determining the mental state of the user 12 may be performed, i.e., the brain activity can be detected in a plurality (e.g., thousands) of separable cortical modules of the user 12, and the full spatial pattern of the brain activity obtained from the cortical modules can be assessed together.

Any one of a variety of models can be used to classify the mental state of the user 12, and will highly depend on the characteristics of brain activity that are input onto the models. Such characteristics of brain activity may typically be extracted from the spatiotemporal brain activity that is captured, and can include, e.g., location of signal, fine grained pattern within or across locations, amplitude of signal, timing of response to behavior, magnitude of frequency bands of the signal (taking the Fourier transform of the time series), ratio of magnitude of frequency bands, cross-correlation between time series of signal between two or more locations captured simultaneously, spectral coherence between two or more locations captured simultaneously, components that maximize variance, components that maximize non-gaussian similarity, etc. The characteristics of brain activity selected to be input into the models must be considered in reference to univariate and multivariate approaches, since the univariate approach, e.g., focuses on a single location, and therefore will not take advantage of features that correlate multiple locations. The characteristics of the brain activity can be extracted from preprocessed raw data recorded during situations of patterns of thought and perception in everyday life, which are characterized by a continually changing stream of consciousness. The preprocessing of the raw data typically involves filtering the data (either in the time domain or the frequency domain) to smooth, remove noise, and separate different components of signal.

Selecting a model will be heavily dependent on whether the data is labeled or unlabeled (meaning is it known what the user is doing at the time that the brain activity is detected), as well as many other factors (e.g., is the data assumed to be normally distributed, is the data assumed relationship linear, is the data assumed relationship non-linear, etc.) Models can include, e.g., support vector machines, expectation maximization techniques, naïve-Bayesian techniques, neural networks, simple statistics (e.g., correlations), deep learning models, pattern classifiers, etc.

These models are typically initialized with some training data (meaning that a calibration routine can be performed on the user to determine what the user is doing). If no training information can be acquired, such models can be heuristically initialized based on prior knowledge, and the models can be iteratively optimized with the expectation that optimization will settle to some optimal maximum or minimum solution. Once it is known what the user is doing, the proper characteristics of the neural activity and proper models can be queried. The models may be layered or staged, so that, e.g., a first model focuses on pre-processing data (e.g., filtering), the next model focuses on clustering the pre-processed data to separate certain features that may be recognized to correlate with a known activity performed by the user, and then the next model can query a separate model to determine the mental state based on that user activity.

As will be described in further detail below, the training data or prior knowledge of the user may be obtained by providing known life/work context to the user. Altogether, the models can be used to track mental state and perception under natural or quasi-natural (i.e., in response to providing known life/work context to the user) and dynamic conditions taking in the time-course of averaged activity and determining the mental state of the user based on constant or spontaneous fluctuations in the characteristics of the brain activity extracted from the data.

A set of data models that have already been proven, for example in a laboratory setting, can be initially uploaded to the mental state awareness system 10, which system will then use the uploaded models to determine the mental state of the user. Optionally, the mental state awareness system 10 may collect data during actual use with the user, which can then be downloaded and analyzed in a separate server, for example in a laboratory setting, to create new or updated models. Software upgrades, which may include the new or updated models, can be uploaded to the mental state awareness system 10 to provide new or updated data modelling and data collection.

Further details regarding determining the mental state of a person based on detected brain activity can be found in a variety of peer-reviewed publications. See, e.g., Lee, B. T., Seok, J. H., Lee., B. C, Cho, S. W., Chai, J. H., Choi, I. G., Ham, B. J., "Neural correlates of affective processing in response to sad and angry facial stimuli in patients with major depressive disorder," Prog Neuropsychopharmacol Biol Psychiatry, 32(3), 778-85 (2008); A. C. Felix-Ortiz, A. C., Burgos-Robles, A., Bhagat, N. D., Leppla, C. A., Tye, K. M., "Bidirectional modulation of anxiety-related and social behaviors by amygdala projections to the medial prefrontal cortex," Neuroscience 321, 197-209 (2016); Beauregard, M., Levesque, J. & Bourgouin, P., "Neural correlates of conscious self-regulation of emotion," J. Neurosci. (2001): 21, RC165; Phan, K. L., Wager, T., Taylor, S. F. & Liberzon, I., "Functional neuroanatomy of emotion: a meta-analysis of emotion activation studies in PET and fMRI," Neuroimage, 16, 331-348 (2002); Canli, T. & Amin, Z., "Neuroimaging of emotion and personality: scientific evidence and ethical considerations," Brain Cogn., 50, 414-431 (2002), McCloskey, M. S., Phan, K. L. & Coccaro, E. F., "Neuroimaging and personality disorders," Curr. Psychiatry Rep., 7, 65-72 (2005); Pridmore, S., Chambers, A. & McArthur, M., "Neuroimaging in psychopathy," Aust. N. Z. J. Psychiatry, 39,856-865 (2005); Heekeren, H. R., Marrett, S., Bandettini, P. A. & Ungerleider, L. G., "A general mechanism for perceptual decision-making in the human brain," Nature, 431,859-862 (2004); Shin L M, Rauch S L, Pitman R K. Amygdala, Medial Prefrontal Cortex, and Hippocampal Function in PTSD, Ann N Y Acad Sci., 1071(1) (2006); Lis E, Greenfield B, Henry M, Guile J M, Dougherty G., "Neuroimaging and genetics of borderline personality disorder: a review," J Psychiatry Neurosci., 32(3), 162-173 (2007); Etkin A, Wager T D, "Functional neuroimaging of anxiety: a meta-analysis of emotional processing in PTSD, social anxiety disorder, and specific phobia," Am J Psychiatry, 164(10), 1476-1488 (2007); Etkin A. Functional Neuroimaging of Major Depressive Disorder: A Meta-Analysis and New Integration of Baseline Activation and Neural Response Data, Am J Psychiatry, 169(7), 693-703 (2012); Sheline Y I, Price J L, Yan Z, Mintun M A, "Resting-state functional MRI in depression unmasks increased connectivity between networks via the dorsal nexus, Proc Natl Acad Sci., 107(24), 11020-11025 (2010); Bari A, Robbins T W, "Inhibition and impulsivity: Behavioral and neural basis of response control," Prog Neurobiol., 108:44-79 (2013); Kagias, Konstantinos et al. "Neuronal responses to physiological stress," Frontiers in genetics, 3:222 (2012).

The mental state awareness system 10 further comprises an optional peripheral life/work context device 16 (e.g., a Smartphone or tablet computer) configured for incorporating known life/work context (e.g., GPS tracking, calendar scheduling, means for listening to music, means for listening to a lecture, means for learning a language, means for engaging in video conversations with others located in remote locations, etc.) to promote, adjust and/or calibrate the experience of the user 12.

For example, based on this known life/work context provided to the user 12 via the peripheral life/work context device 16, the quasi-natural conditions that are contributed to or promoting the actual mental state of the user 12 can be known or better assessed to more accurately determine this mental state.

As another example, the peripheral life/work context device 16 may provide the known life/work context to the user 12 to automatically promote, adjust, regulate, and/or calibrate the mental state of the user, e.g., anxiety, fear, alertness. For example, if the determined mental state of the user 12 is anxiety, then the peripheral life/work context device 16 may change a music selection to a more soothing melody.

The experience of the user 12 can also be individually programmed using a manual selection or manual input on the peripheral life/work context device 16 by the user 12. For example, a variety of individual experiences, such as reading, meditation, taking a nap, watching a television program, watching a live theater or musical performance, or the option for programming any other type of individual experience, can be available from the peripheral life/work context device 16 through a menu of selectable options in order to promote, adjust, regulate and/or calibrate the mental state of the user 12. Such experiences can be selected or individually programed by the user 12, and can be made available through the graphical user interface of the peripheral device 16 though a button, tab, or icon, e.g., through the use of a radio button or similar selectable options, representing one of a set of options of individual experiences.

The mental state awareness system 10 further comprises a biofeedback device 18 configured for automatically providing biofeedback to the user 12 indicative of the mental state determined by the brain interface assembly 14. In the preferred embodiment, the biofeedback device 18 is configured for providing/directing vibrational (or haptic) signals indicative of the determined mental state of the user 12 through peripheral somatosensation, e.g., to areas of the user's 12 skin, e.g., arm, wrist, hand, finger, etc., to provide the user 12 convenient awareness recognition of the determined mental state. The biofeedback device 18 may encode different messages by how the vibrations are constructed or modulated in amplitude or frequency. In one embodiment, the vibrations encode speech, e.g., conversations or speech envelopes, or encode speech at a word level, e.g., single vowel, single word, or a combination of single words and vowels. In another embodiment, the vibration modalities may be encoded to mental state type, level, urgency, or other user-relevant information.

As such, the biofeedback device 18 can serve as brain input through the peripheral nervous (PNS) or sympathetic nervous system (SNS), thereby closing the loop that connects the user's 12 subconscious mental state via brain interfaces by the brain interface assembly 14 to the user's 12 conscious awareness of such mental state. In alternative embodiments, the biofeedback device 18 may be configured for providing/directing audio or visual feedback to the user 12 that may be encoded to signal urgency, levels of mental states, or other user-relevant information, which likewise serves as brain input through the audio or visual nervous system, thereby closing the loop that connects the user's 12 subconscious mental state to the user's 12 conscious awareness of such mental state.

The mental state awareness system 10 also optionally comprises a database, server, or cloud structure 20 configured for tracking the brain activity of the user 12. For example, the database, server, or cloud structure 20 may be configured to collect raw data (e.g., brain activity data) generated by the brain interface assembly 14. Furthermore, the database, server, or cloud structure 20 (independently of or in conjunction with the mental state determination functions of the brain interface assembly 14) may be configured for performing a data analysis of the raw data in order to determine the mental state of the user 12.

For example, if the raw data obtained by the user 12 is being anonym ized and stored in the database, server, or cloud structure 20, the data models can be pooled across various users, which deep learning algorithms would benefit from. The database, server, or cloud structure 20 may be configured for performing cross-correlation analysis of the signal data analysis in order to reduce the pool size of the database and focus subject averaged data to a pool that is similar to the user. Most likely, each user will have a portion of their model optimized to them, but then another portion takes advantage of patterns extracted from a larger pool of users. It should also be appreciated that each user may perform any variety of an infinite number of activities. Thus, even if a user is properly calibrated, such calibration will only be for a small set of infinite possibilities. Generalizing models may comprise various variabilities and optimizing may be difficult. However, by building a large user database on the database, server, or cloud structure 20, a data analysis pipeline connected to such database, server, or cloud structure 20 can preprocess data (clean it up), extract all different kinds of features, and then apply an appropriate data model, to overcome this issue. The brain activity of the user 12 may be tracked with additional life/work context to acquire meta data in depth assessment of awareness and behavior modulation patterns of the user 12. Although, all of the tracked data analysis has been described as being performed by the database, server, or cloud structure 20, it should be appreciated that at least a portion of the tracked data analysis functionality may be incorporated in the peripheral life/work context device 16, with the caveat that it is preferred that the tracking of the brain activity between a pool of users be performed by the database, server, or cloud structure 20.

Having described the structure, function, and application of data models of the mental state awareness system 10, one method 100 of operating the mental state awareness system 10 will now be described.

Initially, the user 12 may have a subconscious mental state (block 102). Such mental state may be, e.g., anxiety, although the user 12 may have other mental states, e.g., focus, attention, creativity, positive or negative reflections/attitude on experiences or the use of objects, the employment of certain critical cognitive brain areas, etc., as discussed above. The anxiety of the user 12 may be broken down into a specific experience (block 104), e.g., anxiety about a thing (block 104*a*), e.g., rent, mortgage, or credit card payment is due, anxiety about a topic (block 104*b*), e.g., concerned over the well-being of a parent, being interviewed, presenting or acting in front of an audience, or anxiety about fear (block 104*c*), e.g., fear of darkness in unfamiliar spaces, fear of aircraft travel, fear of ocean liner travel, fear of heights. The peripheral life/work context device 16 may incorporate additional life/work context into the experience of the user 12 (e.g., GPS tracking, calendar scheduling, means for listening to music, means for listening to a lecture, means for learning a language, means for engaging in video conversations with others located in remote locations, etc.) (block 106). It should be appreciated that, although the additional life/work context is illustrated as being provided to the user 12 after or during the initial experience that results in the mental state, the additional life/work context can be provided to the user 12 at any time during the method 100.

The brain interface assembly 14 detects the brain activity of the user 12 (block 108). For example, the brain interface assembly 14 may detect energy (e.g., optical energy or magnetic energy) from the brain and through the skull of the user 12, and determine the brain activity in response to detecting the energy from the brain of the user 12. The brain interface assembly 14 (or alternatively, the database, server, or cloud structure 20) then determines the mental state of a user 12 (in this case, anxiety) based on the detected brain activity (block 110).

The biofeedback device 16 then provides biofeedback to the user 12 indicative of the determined mental state of the user 12 caused by any one of the experiences (block 112). For example, the biofeedback device 16 may provide/direct vibrational signals to the user 12 indicative of the determined mental state of the user 12 through peripheral somatosensation, e.g., vibrational signals encoded with one or more messages, or alternatively, may provide/direct audio or visual signals to the user 12 indicative of the determined mental state of the user 12. Thus, input is provided to the brain of the user 12 to make the user 12 aware of his or her mental state, thereby closing the loop on the experience 108 (block 114). As such, the user 12 may regulate, adjust, and/or calibrate his or her emotions or make more objective decisions (block 116). Furthermore, the peripheral life/work context device 16 may automatically regulate, adjust and/or calibrate the experience of the user 12 based on the determined mental state of the user 12 by, e.g., playing soothing music (block 118).

Figure 3:
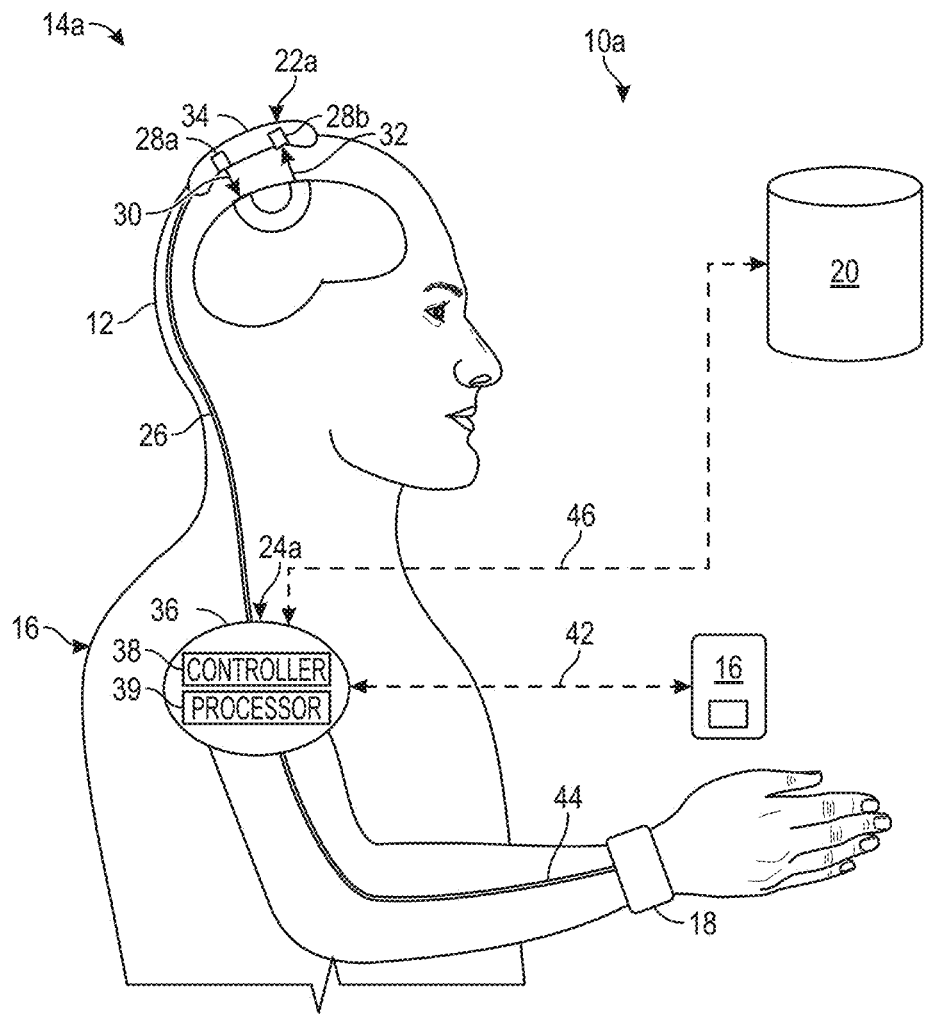
FIG. 3 is a view of one specific embodiment of the non-invasive mental state awareness system of FIG. 1.

Referring to FIG. 3, one particular embodiment of a mental state awareness system 10*a* will now be described. The mental state awareness system 10*a* comprises an optically-based non-invasive brain interface assembly 14*a*, which may, e.g., incorporate any one or more of the neural activity detection technologies described in U.S. patent application Ser. No. 15/844,370, entitled "Pulsed Ultrasound Modulated Optical Tomography Using Lock-In Camera,"

U.S. patent application Ser. No. 15/844,398, entitled "Pulsed Ultrasound Modulated Optical Tomography With Increased Optical/Ultrasound Pulse Ratio," U.S. patent application Ser. No. 15/844,411, entitled "Optical Detection System For Determining Neural Activity in Brain Based on Water Concentration," U.S. patent application Ser. No. 15/853,209, entitled "System and Method For Simultaneously Detecting Phase Modulated Optical Signals," U.S. patent application Ser. No. 15/853,538, entitled "Systems and Methods For Quasi-Ballistic Photon Optical Coherence Tomography In Diffusive Scattering Media Using a Lock-In Camera" (now U.S. Pat. No. 10,219,700), U.S. patent application Ser. No. 16/266,818, entitled "Ultrasound Modulating Optical Tomography Using Reduced Laser Pulse Duration," U.S. Provisional Patent Application Ser. No. 62/657,634, entitled "Balanced Holography Technique For Imaging In Highly Scattering Medium," U.S. Provisional Patent Application Ser. No. 62/692,074, entitled "Frequency Domain Optical Spectroscopy For Neural Decoding," U.S. Provisional Patent Application Ser. No. 62/667,770, entitled "Ultrasound-Mediated Optical Detection," U.S. Provisional Patent Application Ser. No. 62/692,124, entitled "Interferometric Frequency-Swept Source And Detector In A Photonic Integrated Circuit," U.S. Provisional Patent Application Ser. No. 62/726,168, entitled "Single-Shot Spectral-Domain Interferometric Near-Infrared Spectroscopy Based On Orthogonal Dispersion, U.S. Provisional Patent Application Ser. No. 62/719,509, entitled "Interferometric Parallel Detection Of Multiple-Scattered Light With Swept Source Illumination," U.S. Provisional Patent Application Ser. No. 62/740,814, entitled "Coherence Gated Diffuse Correlation Spectroscopy Neural Decoding," U.S. Provisional Patent Application Ser. No. 62/722,152, entitled "Time-Of-Flight Optical Measurement And Decoding Of Fast-Optical Signals," U.S. Provisional Patent Application Ser. No. 62/781,098, entitled "Detection Of Fast-Neural Signal Using Depth-Resolved Spectroscopy," U.S. patent application Ser. No. 16/226,625, entitled "Spatial and Temporal-Based Diffusive Correlation Spectroscopy Systems and Methods," and U.S. Provisional Patent Application Ser. No. 62/772,584, entitled "Diffuse Correlation Spectroscopy Measurement Systems and Methods," which are all expressly incorporated herein by reference.

The brain interface assembly 14a includes a wearable unit 22a configured for being applied to the user 12, and in this case, worn on the head of the user 12; and an auxiliary head-worn or non-head-worn unit 24a (e.g., worn on the neck, shoulders, chest, or arm). Alternatively, the functionality of the unit 24a may be incorporated into the head-worn unit 22a. The auxiliary non-head-worn unit 24a may be coupled to the head-worn unit 22a via a wired connection 26 (e.g., electrical wires). Alternatively, the brain interface assembly 14a may use a non-wired connection (e.g., wireless radio frequency (RF) signals (e.g., Bluetooth, Wifi, cellular, etc.) or optical links (e.g., fiber optic or infrared (IR)) for providing power to or communicating between the respective head-worn unit 22a and the auxiliary unit 24a.

The head-worn unit 22a comprises electronic or optical components, such as, e.g., one or more optical sources, an interferometer, one or more optical detector(s) (not shown), etc., an output port 28a for emitting sample light 30 generated by the brain interface assembly 14a into the head of the user 12, an input port 28b configured for receiving neural-encoded signal light 32 from the head of the user 12, which signal light is then detected, modulated and/or processed to determine neural activity within the brain of the user 12, and a support housing structure 34 containing the electronic or optical components, and ports 28a, 28b.

The support housing structure 34 may be shaped, e.g., have a banana, headband, cap, helmet, beanie, other hat shape, or other shape adjustable and conformable to the user's head, such that the ports 28a, 28b are in close contact with the outer skin of the head, and in this case, the scalp of the user 12. The support housing structure 34 may be made out of any suitable cloth, soft polymer, plastic, hard shell, and/or any other suitable material as may serve a particular implementation. In an alternative embodiment, optical fibers (not shown) may be respectively extended from the ports 28a, 28b, thereby freeing up the requirement that the ports 28a, 28b be disposed in close proximity to the surface of the head. In any event, an index matching fluid may be used to reduce reflection of the light generated by the head-worn unit 22a from the outer skin of the scalp. An adhesive, strap, or belt (not shown) can be used to secure the support housing structure 34 to the head of the user 12.

The auxiliary unit 24a comprises a housing 36 containing a controller 38 and a processor 40. The controller 38 is configured for controlling the operational functions of the head-worn unit 22a, whereas the processor 40 is configured for processing the neural-encoded signal light 32 acquired by the head-worn unit 22a to detect and localize the neural activity within the brain of the user 12. The auxiliary unit 24a may additionally include a power supply (which if head-worn, may take the form of a rechargeable or non-chargeable battery), a control panel with input/output functions, a display, and memory. Alternatively, power may be provided to the auxiliary unit 24a wirelessly (e.g., by induction).

The functionalities of the peripheral life/work context device 16, biofeedback device 18, and database, server, or cloud structure 20 may be the same as described above with respect to FIG. 1.

The peripheral life/work context device 16 is coupled to the auxiliary unit 24a of the brain interface assembly 14a (and/or the biofeedback device 18) via a wireless connection 42 (e.g., wireless radio frequency (RF) signals (e.g., Bluetooth, Wifi, cellular, etc.) or optical links (e.g., fiber optic or infrared (IR)) for communicating between the peripheral life/work context device 16 and the brain interface assembly 14a (and/or the biofeedback device 18). Alternatively, a wired connection between the peripheral life/work context device 16 and the brain interface assembly 14a (and/or the biofeedback device 18) may be used.

The biofeedback device 18 is coupled to the brain interface assembly 14a (and in this case, to the auxiliary unit 24a) via a wired connection 44 (e.g., electrical wires). Alternatively, a non-wired connection (e.g., wireless radio frequency (RF) signals (e.g., Bluetooth, Wifi, cellular, etc.) or optical links (e.g., fiber optic or infrared (IR)) for providing power to or communicating between the respective the auxiliary unit 24a of the brain interface assembly 14a and the biofeedback device 18 may be used.

The database, server, or cloud structure 20 may be coupled to the auxiliary unit 24a of the brain interface assembly 14a (and/or the peripheral life/work context device 16 and biofeedback device 18) via a wireless connection 46 (e.g., wireless radio frequency (RF) signals (e.g., Bluetooth, Wifi, cellular, etc.) or optical links (e.g., fiber optic or infrared (IR)) for providing power to or communicating between the biofeedback device 18 and the database, server or cloud structure 20. Alternatively, a wired connection between the database, server, or cloud structure 20 and the auxiliary unit 24a of the brain interface assembly 14a (and/or the peripheral life/work context device 16 and biofeedback device 18) may be used.

Figure 4:
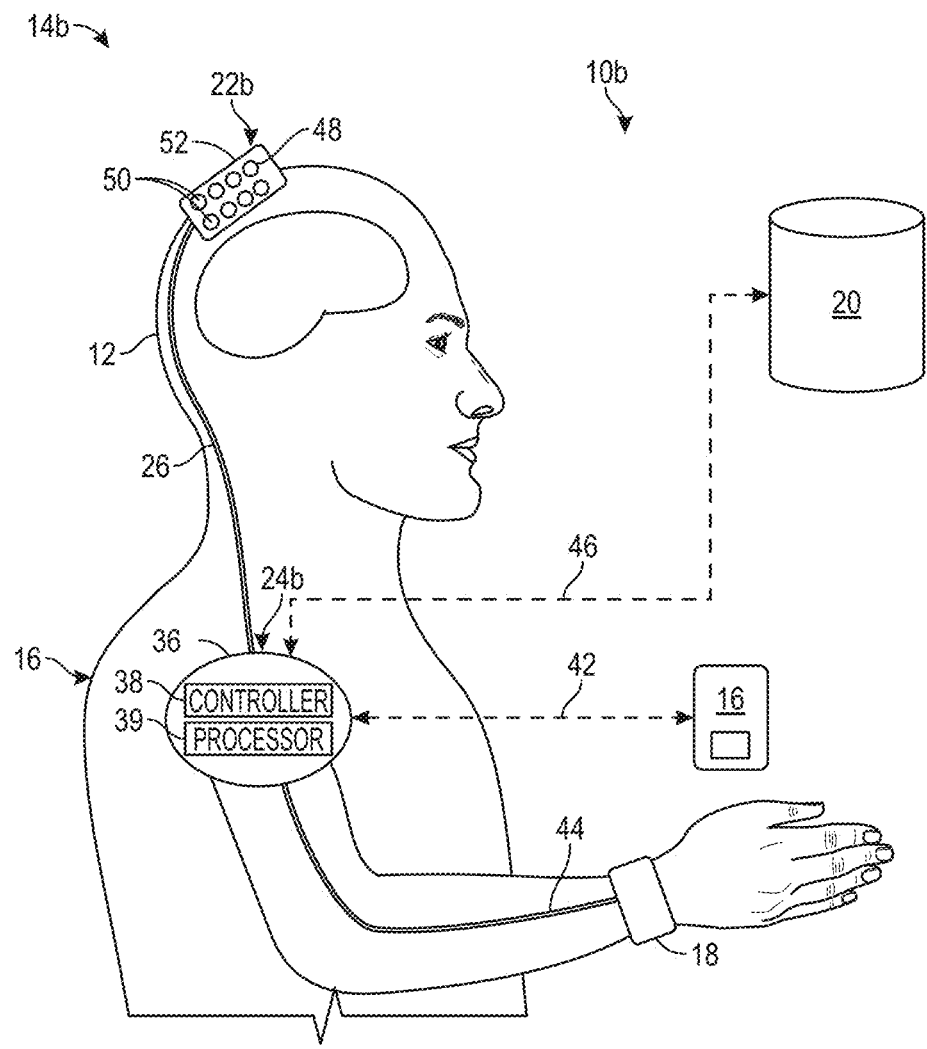
FIG. 4 is a view of another specific embodiment of the mental state awareness system of FIG. 1.

Referring to FIG. 4, another particular embodiment of a mental state awareness system 10b will now be described. The mental state awareness system 10b comprises an optically-based non-invasive brain interface assembly 14b, which may, e.g., incorporate any one or more of the neural activity detection technologies described in U.S. Non-Provisional patent application Ser. No. 16/051,462, entitled "Fast-Gated Photodetector Architecture Comprising Dual Voltage Sources with a Switch Configuration" (now U.S. Pat. No. 10,158,038), U.S. patent application Ser. No. 16/202,771, entitled "Non-Invasive Wearable Brain Interface Systems Including a Headgear and a Plurality of Self-Contained Photodetector Units Configured to Removably Attach to the Headgear," and U.S. patent application Ser. No. 16/283,730, entitled "Stacked Photodetector Assemblies," which are all expressly incorporated herein by reference.

The brain interface assembly 14b includes a head-worn unit 22b that is configured for being applied to the user 12, and in this case, worn on the head of the user 12; and an auxiliary non-head-worn unit 24b (e.g., worn on the neck, shoulders, chest, or arm). Alternatively, the functionality of the unit 24b may be incorporated into the head-worn unit 22b, as described below. The auxiliary non-head-worn unit 24b may be coupled to the head-worn unit 22b via a wired connection 26 (e.g., electrical wires). Alternatively, the brain interface assembly 14b may use a non-wired connection (e.g., wireless radio frequency (RF) signals (e.g., Bluetooth, Wifi, cellular, etc.) or optical links (e.g., fiber optic or infrared (IR)) for providing power to or communicating between the respective head-worn unit 22b and the auxiliary unit 24b.

The head-worn unit 22b includes one or more light sources 48 configured for generating light pulses. The light source(s) 48 may be configured for generating one or more light pulses at one or more wavelengths that may be applied to a desired target (e.g., a target within the brain). The light source(s) 48 may be implemented by any suitable combination of components. For example, light source(s) 48 described herein may be implemented by any suitable device. For example, a light source as used herein may be, for example, a distributed feedback (DFB) laser, a super luminescent diode (SLD), a light emitting diode (LED), a diode-pumped solid-state (DPSS) laser, a laser diode (LD), a super luminescent light emitting diode (sLED), a vertical-cavity surface-emitting laser (VCSEL), a titanium sapphire laser, a micro light emitting diode (mLED), and/or any other suitable laser or light source.

The head-worn unit 22b includes a plurality of photodetector units 50, e.g., comprising single-photon avalanche diodes (SPADs) configured for detecting a single photon (i.e., a single particle of optical energy) in each of the light pulses. For example, an array of these sensitive photodetector units can record photons that reflect off of tissue within the brain in response to application of one or more of the light pulses generated by the light sources 48. Based on the time it takes for the photons to be detected by the photodetector units, neural activity and other attributes of the brain can be determined or inferred.

Photodetector units that employ the properties of a SPAD are capable of capturing individual photons with very high time-of-arrival resolution (a few tens of picoseconds). When photons are absorbed by a SPAD, their energy frees bound charge carriers (electrons and holes) that then become free-carrier pairs. In the presence of an electric field created by a reverse bias voltage applied to the diode, these free-carriers are accelerated through a region of the SPAD, referred to as the multiplication region. As the free carriers travel through the multiplication region, they collide with other carriers bound in the atomic lattice of the semiconductor, thereby generating more free carriers through a process called impact ionization. These new free-carriers also become accelerated by the applied electric field and generate yet more free-carriers. This avalanche event can be detected and used to determine an arrival time of the photon. In order to enable detection of a single photon, a SPAD is biased with a reverse bias voltage having a magnitude greater than the magnitude of its breakdown voltage, which is the bias level above which free-carrier generation can become self-sustaining and result in a runaway avalanche. This biasing of the SPAD is referred to as arming the device. When the SPAD is armed, a single free carrier pair created by the absorption of a single photon can create a runaway avalanche resulting in an easily detectable macroscopic current.

It will be recognized that in some alternative embodiments, the head-worn unit 22b may include a single light source 48 and/or single photodetector unit 50. For example, brain interface system 14b may be used for controlling a single optical path and for transforming photodetector pixel measurements into an intensity value that represents an optical property of a brain tissue region. In some alternative embodiments, the head-worn unit 22b does not include individual light sources. Instead, a light source configured to generate the light that is detected by the photodetector may be included elsewhere in the brain interface system 14b. For example, a light source may be included in the auxiliary unit 24b.

The head-worn unit 22b further comprises a support housing structure 52 containing the light source(s) 48, photodetector units 50, and other electronic or optical components. As will be described in further detail below, the support housing structure 52 may be shaped, e.g., have a banana, headband, cap, helmet, beanie, other hat shape, or other shape adjustable and conformable to the user's head, such that the photodetector units 50 are in close contact with the outer skin of the head, and in this case, the scalp of the user 12. The support housing structure 52 may be made out of any suitable cloth, soft polymer, plastic, hard shell, and/or any other suitable material as may serve a particular implementation.

The auxiliary unit 24b comprises the housing 36 containing the controller 38 and the processor 40. The controller 38 is configured for controlling the operational functions of the head-worn unit 22b, whereas the processor 40 is configured for processing the photons acquired by the head-worn unit 22b to detect and localize the neural activity within the brain of the user 12. The auxiliary unit 24b may additionally include a power supply (which if head-worn, may take the form of a rechargeable or non-chargeable battery), a control panel with input/output functions, a display, and memory. Alternatively, power may be provided to the auxiliary unit 24b wirelessly (e.g., by induction).

The functionalities of the peripheral life/work context device 16, biofeedback device 18, and database, server, or cloud structure 20 may be the same as described above with respect to FIG. 1.

The peripheral life/work context device 16 is coupled to the auxiliary unit 24b of the brain interface assembly 14b (and/or the biofeedback device 18) via a wireless connection 42 (e.g., wireless radio frequency (RF) signals (e.g., Bluetooth, Wifi, cellular, etc.) or optical links (e.g., fiber optic or infrared (IR)) for communicating between the peripheral life/work context device 16 and the brain interface assembly 14b (and/or the biofeedback device 18). Alternatively, a wired connection between the peripheral life/work context device 16 and the brain interface assembly 14c (and/or the biofeedback device 18) may be used.

The biofeedback device 18 is coupled to the brain interface assembly 14b (and in this case, to the auxiliary unit 24b) via a wired connection 44 (e.g., electrical wires). Alternatively, a non-wired connection (e.g., wireless radio frequency (RF) signals (e.g., Bluetooth, Wifi, cellular, etc.) or optical links (e.g., fiber optic or infrared (IR)) for providing power to or communicating between the respective the auxiliary unit 24b of the brain interface assembly 14c and the biofeedback device 18 may be used.

The database, server, or cloud structure 20 may be coupled to the auxiliary unit 24b of the brain interface assembly 14b (and/or the peripheral life/work context device 16 and biofeedback device 18) via a wireless connection 46 (e.g., wireless radio frequency (RF) signals (e.g., Bluetooth, Wifi, cellular, etc.) or optical links (e.g., fiber optic or infrared (IR)) for providing power to or communicating between the biofeedback device 18 and the database, server or cloud structure 20. Alternatively, a wired connection between the database, server, or cloud structure 20 and the auxiliary unit 24b of the brain interface assembly 14b (and/or the peripheral life/work context device 16 and biofeedback device 18) may be used.

Referring now to FIGS. 5A-5D, different embodiments of the brain interface assembly 14b will be described. Such brain interface assemblies 14b may communicate wirelessly or via wire with the peripheral life/work context device 16, biofeedback device 18, and database, server, cloud structure 20, as described above. Each of the brain interface assemblies 14b described below comprises a head-worn unit 22b having a plurality of photodetector units 50 and a support housing structure 52 in which the photodetector units 50 are embedded. Each of the photodetector units 50 may comprise, e.g., a SPAD, voltage sources, capacitors, switches, and any other circuit components (not shown) required to detect photons. Each of the brain interface assemblies 14b may also comprise one or more light sources (not shown) for generating light pulses, although the source of such light may be derived from ambient light in some cases. Each of brain interface assemblies 14b may also comprise a control/processing unit 54, such as, e.g., a control circuit, time-to-digital (TDC) converter, and signal processing circuit for controlling the operational functions of the photodetector units 50 and any light source(s), and processing the photons acquired by photodetector units 50 to detect and localize the neural activity within the brain of the user 12. As will be described in further detail below, the control/processing unit 54 may be contained in the head-worn unit 22b or may be incorporated into a self-contained auxiliary unit. As will be set forth below, the support housing structure 52 may be shaped, e.g., have a banana, headband, cap, helmet, beanie, other hat shape, or other shape adjustable and conformable to the user's head, such that the photodetector units 50 are in close contact with the outer skin of the head, and in this case, the scalp of the user 12.

Figure 5A:
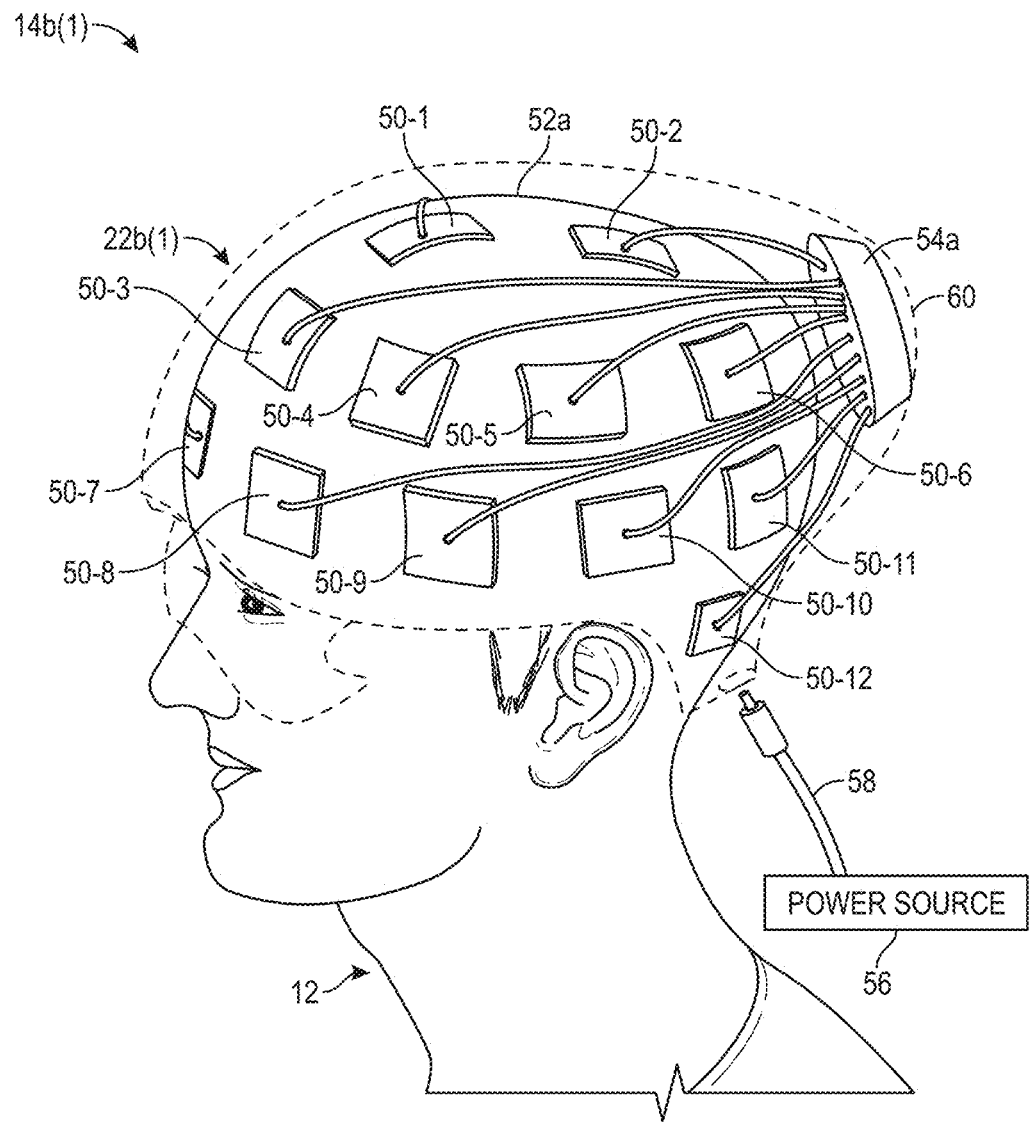
FIG. 5A-5D illustrate exemplary non-invasive wearable devices as used with the system of FIG. 4.

As shown in FIG. 5A, a brain interface assembly 14b(1) comprises a head-worn unit 22b(1) and a power source 56 coupled to the head-worn unit 22b(1) via a power cord 58. The head-worn unit 22b(1) includes the photodetector units 50 (shown as 50-1 through 50-12) and a master control unit 54a. The head-worn unit 22b(1) further includes a support housing structure 52a that takes a form of a cap that contains the photodetector units 50 and master control unit 54a. The material for the cap 52a may be selected out of any suitable cloth, soft polymer, plastic, hard shell, and/or any other suitable material as may serve a particular implementation. The power source 56 may be implemented by a battery and/or any other type of power source configured to provide operating power to the photodetector units 50, master control unit 54a, and any other component included within the brain interface assembly 22b(1) via the power cord 58. The head-worn unit 22b(1) optionally includes a crest or other protrusion 60 formed in the cap 52a for providing means of carrying a control/processing unit 54a.

Figure 5B:
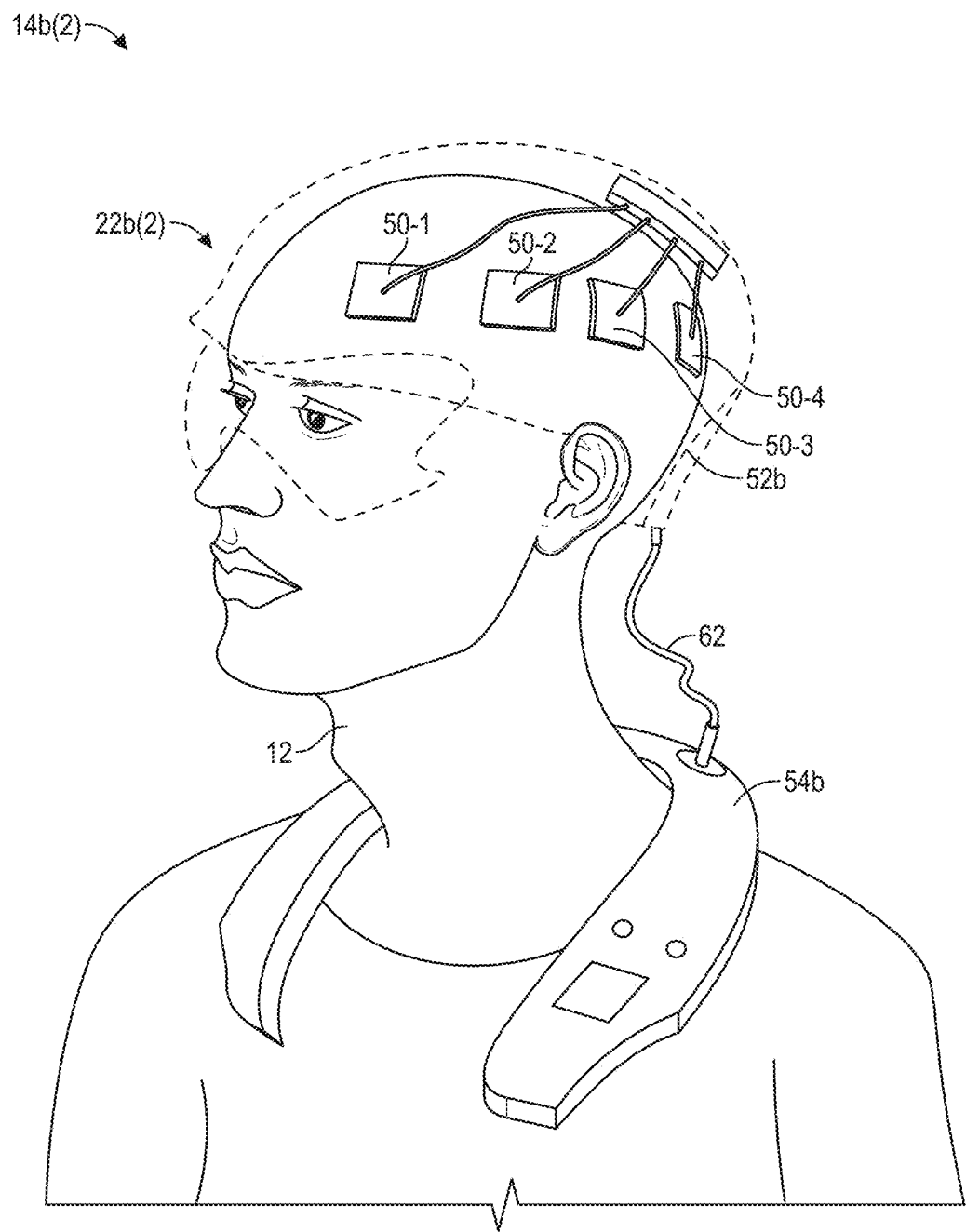

As shown in FIG. 5B, a brain interface assembly 14b(2) comprises a head-worn unit 22b(2) and a master control unit 54b coupled to the head-worn unit 22b(2) via a wired connection 62. The head-worn unit 22b(2) includes the photodetector units 50 (shown as 50-1 through 50-4), and a support housing structure 52b that takes a form of a helmet containing the photodetector units 50. The material for the helmet 52b may be selected out of any suitable polymer, plastic, hard shell, and/or any other suitable material as may serve a particular implementation. Unlike the master control unit 54a of the brain interface assembly 14b(1) illustrated in FIG. 5A, which is contained in the head-worn unit 22b(1), the master control unit 54b is self-contained, and may take the form of a garment (e.g., a vest, partial vest, or harness) for being worn on the shoulders of the user 12. The self-contained master control unit 54b may additionally include a power supply (which if head-worn, may take the form of a rechargeable or non-chargeable battery), a control panel with input/output functions, a display, and memory. Alternatively, power may be provided to the self-contained master control unit 54b wirelessly (e.g., by induction).

Figure 5C:
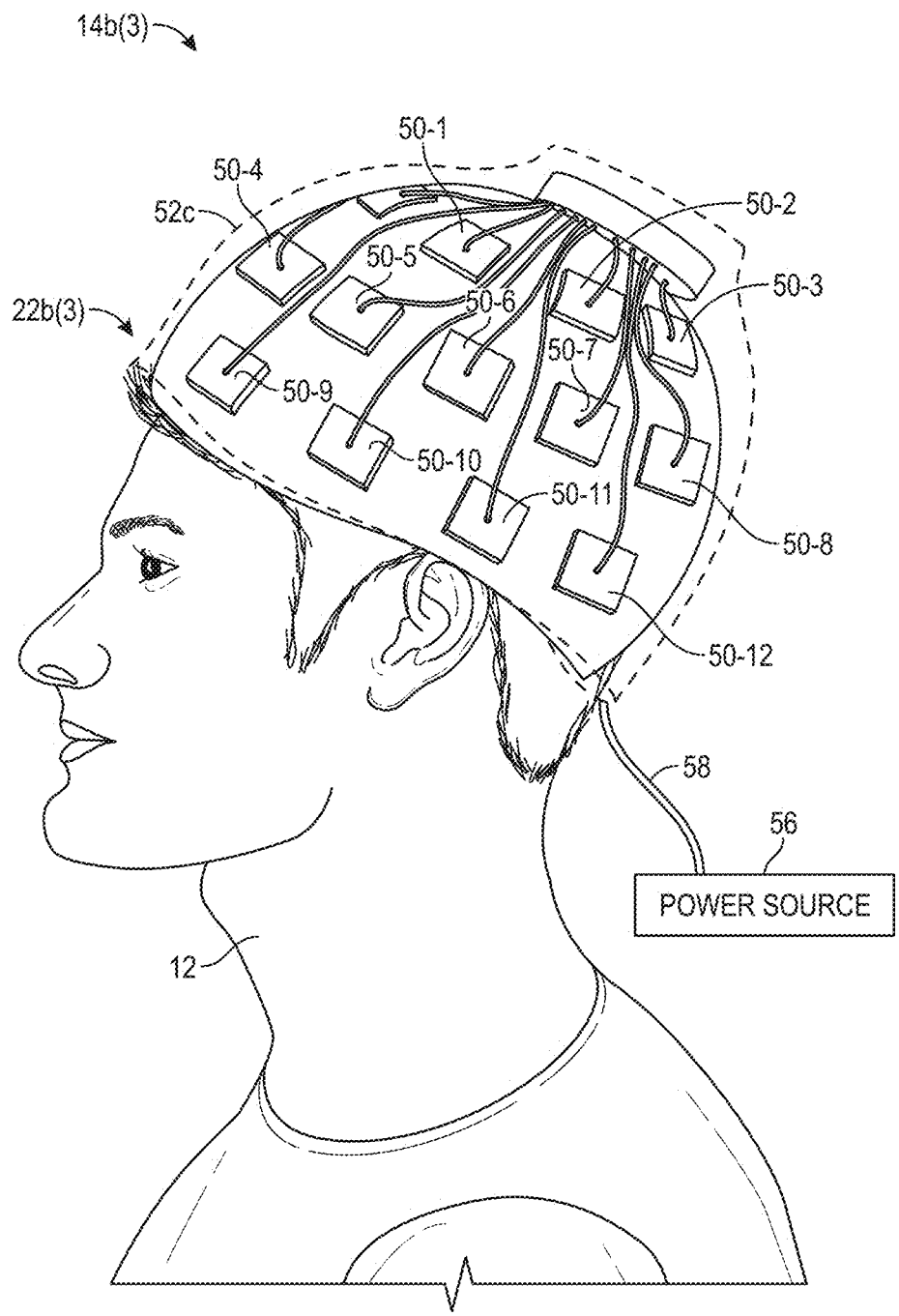

As shown in FIG. 5C, a brain interface assembly 14b(3) comprises a head-worn unit 22b(3) and a power source 56 coupled to the head-worn unit 22b(3) via a power cord 74. The head-worn unit 22b(3) includes the photodetector units 50 (shown as 50-1 through 50-12) and a master control 54c. The head-worn unit 22b(3) further includes a support housing structure 52c that takes a form of a beanie that contains the photodetector units 50 and master control 54c. The material for the beanie 68c may be selected out of any suitable cloth, soft polymer, plastic, and/or any other suitable material as may serve a particular implementation. The power source 56 may be implemented by a battery and/or any other type of power source configured to provide operating power to the photodetector units 50, master control 54c, and any other component included within the brain interface assembly 22b(3) via a wired connection 58.

Figure 5D:
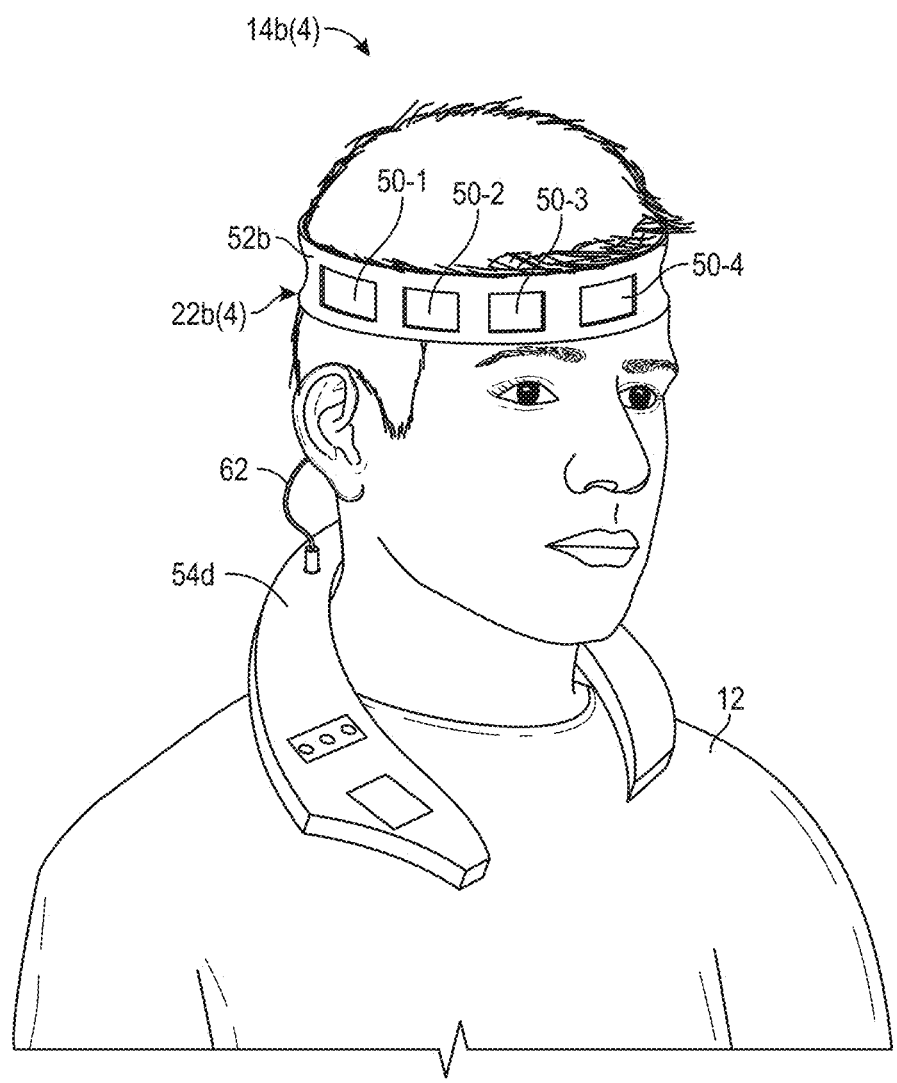

As shown in FIG. 5D, a brain interface assembly 14b(4) comprises a head-worn unit 22b(4) and a master control 54d coupled to the head-worn unit 22b(4) via a wired connection 62. The head-worn unit 22b(4) includes the photodetector units 50 (shown as 50-1 through 50-4), and a support housing structure 52d that takes a form of a headband containing the photodetector units 50. The material for the headband 52d may be selected out of any suitable cloth, soft polymer, plastic, hard shell, and/or any other suitable material as may serve a particular implementation. The master control 54d is self-contained, and may take the form of a garment (e.g., a vest, partial vest, or harness) for being worn on the shoulders of the user 12. The self-contained master control 54d may additionally include a power supply (which if head-worn, may take the form of a rechargeable or non-chargeable battery), a control panel with input/output functions, a display, and memory. Alternatively, power may be provided to the self-contained master control 54d wirelessly (e.g., by induction).

Figure 8:
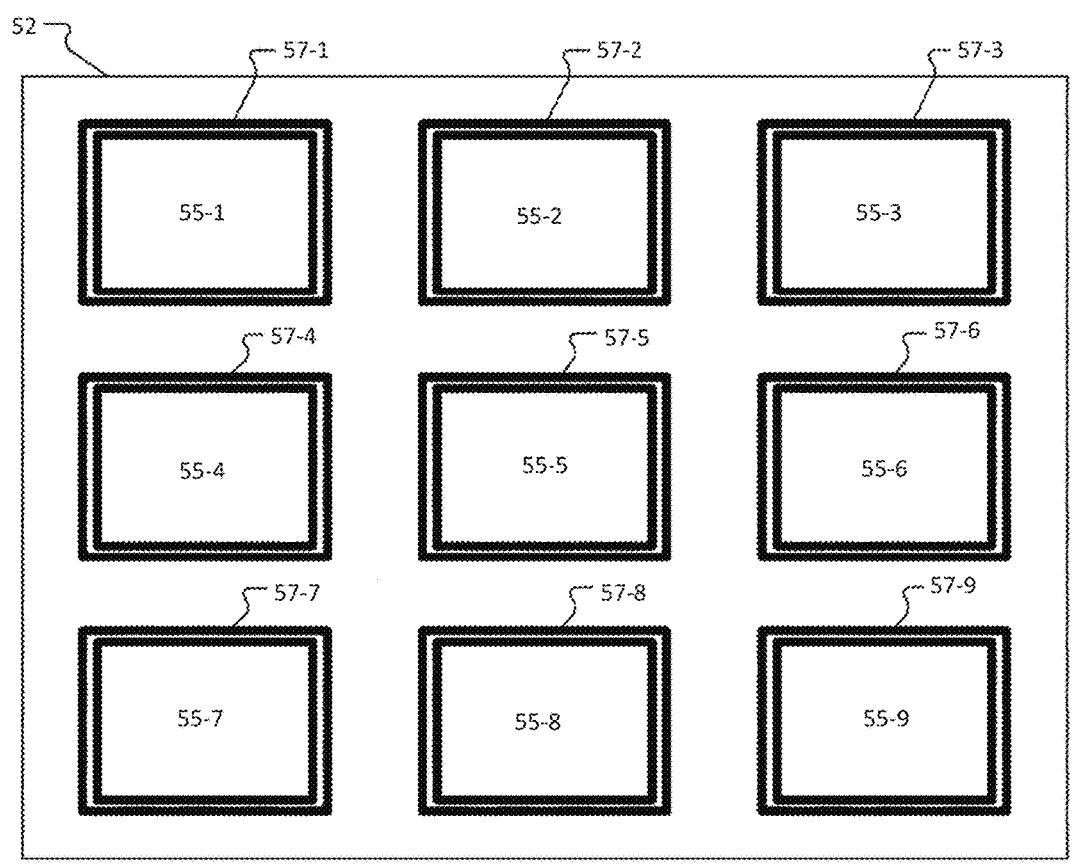
FIG. 8 is a plan view illustrating cutouts for photodetector units in any of the exemplary non-invasive wearable devices of FIGS. 5A-5D.

In any of the embodiments illustrated in FIGS. 5A-5D, the photodetector units 50 may be attached the support housing structures 52a-d in any suitable manner. For example, any of the support housing structures 52a-d may include a plurality of cutouts within which the photodetector units 50 are configured to fit, a plurality of protrusions on an inner surface of the support housing structure 52a-d to which the photodetector units are configured to attached, a plurality of embedded housings configured to enclose individual photodetector units 50, and/or any other suitable attachment mechanism or element. For example, as illustrated in FIG. 8, an exemplary portion of any of the support housing structures 52a-d that includes a plurality of cutouts 55 (e.g., cutout 55-1 through cutout 55-9). In FIG. 8, the photodetector units 50 have not yet been inserted within cutouts 55. As shown, each cutout 55 may be surrounded by a rigid ring 57 embedded within the support housing structure 52a-d. For example, the cutout 55 is surrounded by the rigid ring 57. The rigid rings 57 may be made out of any suitable material (e.g., plastic, metal, etc.). The rigid rings 57 may include one or more grooves or other features configured to facilitate removable attachment of the photodetector units 50 to the support housing structure 52a-d. While the cutouts 55 and rigid rings 57 are shown in FIG. 8 to be rectangular, the cutouts 55 and rigid rings 57 may alternatively be any other shape and/or size.

Each photodetector unit 50 may be self-contained. In other words, each photodetector unit 50 may be housed within its own casing. Each photodetector unit 50 may include an individual light source configured to generate light and a plurality of photodetectors configured to detect photons of the light after the photons reflect from a target within a brain of the user 12. In some examples, each photodetector unit 50 may include a printed circuit board on which the light source and the photodetectors are disposed. In some alternative embodiments, each photodetector unit 50 does not include individual light sources. Instead, a light source configured to generate the light that is detected by the photodetector units 50 may be included elsewhere. For example, a light source may be included in the master control unit 54 and coupled to the photodetector units 50 through electrical connections.

The master control unit 54 is communicatively coupled to each of photodetector units 50 by way of a plurality of wires. In some examples, the wires are at least partially tunneled from the photodetector units 50 to the master control unit 54 within a material of the support housing structure 52. In some examples, each photodetector unit 50 includes a plug interface configured to connect to one or more of the wires. The master control unit 54 may be configured to control the photodetector units 50. For example, the master control unit 54 may direct the light source of each photodetector unit 50 to generate the light in the photodetectors of each photodetector unit 50 to detect the photons of the light. As shown, the master control unit 54 is located within the support housing structure 52. In alternative embodiments, the master control unit 54 may be configured to be worn off the head of user 12. In some examples, the master control unit 54 may be selectively removed from the support housing structure 52.

Figure 6:
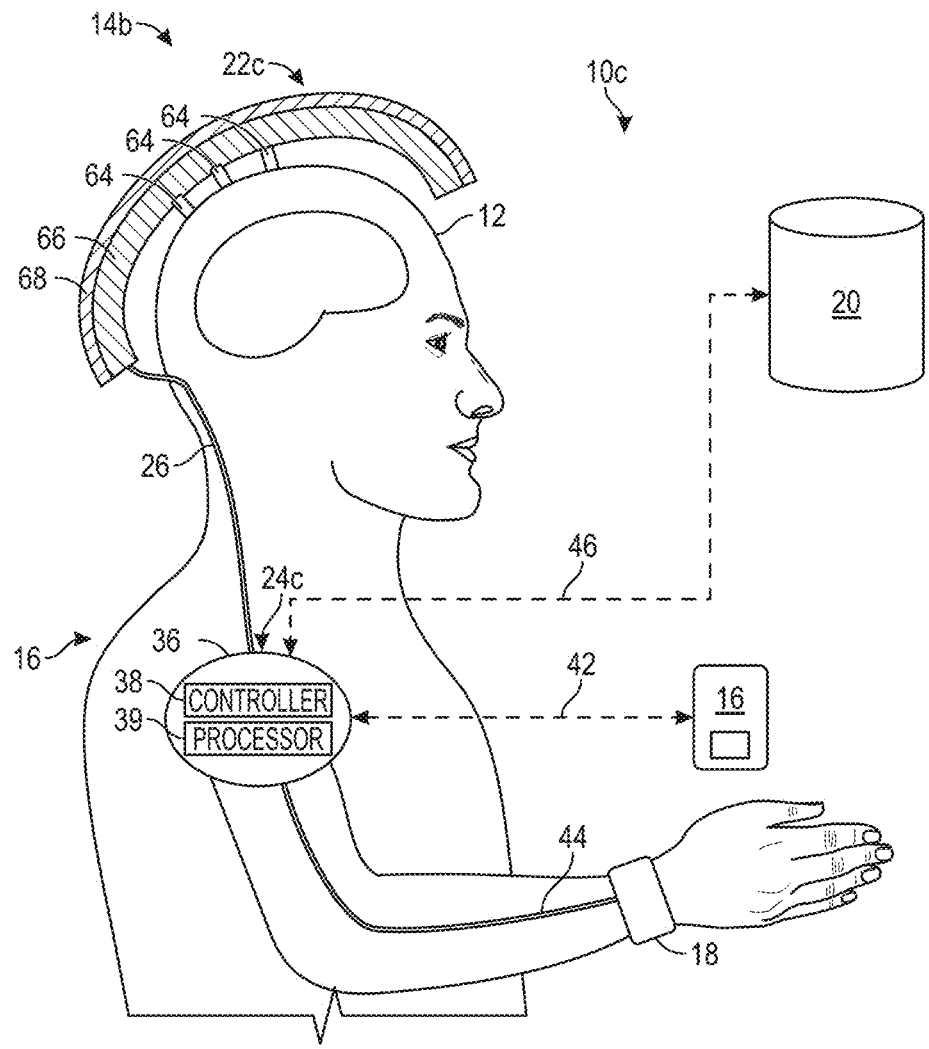
FIG. 6 is a view of still another specific embodiment of the mental state awareness system of FIG. 1.

Referring to FIG. 6, still another particular embodiment of a mental state awareness system 10c will now be described. The mental state awareness system 10c comprises a magnetically-based non-invasive brain interface assembly 14c, which may, e.g., incorporate any one or more of the neural activity detection technologies described in U.S. Provisional Patent Application Ser. No. 62/689,696, entitled "Magnetic Field Measurement Systems and Methods of Making and Using," U.S. Provisional Patent Application Ser. No. 62/732,327, entitled "Variable Dynamic Range Optical Magnetometer and Methods of Making and Using", U.S. Provisional Patent Application Ser. No. 62/741,777, entitled, "Integrated Gas Cell and Optical Components for Atomic Magnetometry and Methods for Making and Using," U.S. Provisional Patent Application Ser. No. 62/752,067, entitled "Magnetic Field Shaping Components for Magnetic Field Measurement Systems and Methods for Making and Using," U.S. patent application Ser. No. 16/213,980, entitled "Systems and Methods Including Multi-Mode Operation of Optically Pumped Magnetometer(S)," U.S. Provisional Patent Application Ser. No. 62/732,791, entitled "Dynamic Magnetic Shielding and Beamforming Using Ferrofluid for Compact Magnetoencephalography (MEG)," U.S. Provisional Patent Application Ser. No. 62/796,958, entitled "Optically Pumped Magnetometer with Amplitude-Selective Magnetic Shield," and U.S. Provisional Patent Application Ser. No. 62/804,539, entitled "Neural Bandpass Filters for Enhanced Dynamic Range Magnetoencephalography (MEG) Systems and Methods," which are all expressly incorporated herein by reference.

The brain interface assembly 14c includes a magnetoencephalography (MEG) head-worn unit 22c that is configured for being applied to the user 12, and in this case, worn on the head of the user 12; and an auxiliary non-head-worn unit 24c (e.g., worn on the neck, shoulders, chest, or arm). Alternatively, the functionality of the unit 24c may be incorporated into the head-worn unit 22c, as described below. The auxiliary non-head-worn unit 24c may be coupled to the head-worn unit 22c via a wired connection 26 (e.g., electrical wires). Alternatively, the brain interface assembly 14c may use a non-wired connection (e.g., wireless radio frequency (RF) signals (e.g., Bluetooth, Wifi, cellular, etc.) or optical links (e.g., fiber optic or infrared (IR)) for providing power to or communicating between the respective head-worn unit 22c and the auxiliary unit 24c.

The head-worn unit 22c includes a plurality of optically pumped magnetometers (OPMs) 64 or other suitable magnetometers to measure biologically generated magnetic fields from the brain of the user 12 and a passive shield 66 (and/or flux concentrators). By placing the passive shield 66 over the head of the user 12, the ambient background magnetic field arising from areas outside the passive shield 66 is greatly decreased and the magnetometers 64 can measure or detect magnetic fields from activity occurring in the brain of the user 12 due to the reduction in the ambient background magnetic field.

An OPM is an optical magnetometry system used to detect a magnetic field that propagates through the human head. Optical magnetometry can include the use of optical methods to measure a magnetic field with very high accuracy—on the order of $1 \times 10^{-15}$ Tesla. Of particular interest for their high-sensitivity, an OPM can be used in optical magnetometry to measure weak magnetic fields. (The Earth's magnetic field is typically around 50 micro Tesla). In at least some systems, the OPM has an alkali vapor gas cell that contains alkali metal atoms in a combination of gas, liquid, or solid states (depending on temperature). The gas cell may contain a quenching gas, buffer gas, or specialized anti-relaxation coatings or any combination thereof. The size of the gas cells can vary from a fraction of a millimeter up to several centimeters, allowing the practicality of OPMs to be used with wearable non-invasive brain interface devices. The head-worn unit 22c further comprises a support housing structure 68 containing the OPMs 64, passive shield 66, and other electronic or magnetic components. As will be described in further detail below, the support housing structure 84 may be shaped, e.g., have a banana, headband, cap, helmet, beanie, other hat shape, or other shape adjustable and conformable to the user's head, such that the OPMs 64 are in close contact with the outer skin of the head, and in this case, the scalp of the user 12. The support housing structure 68 may be made out of any suitable cloth, soft polymer, plastic, hard shell, and/or any other suitable material as may serve a particular implementation.

The auxiliary unit 24c comprises the housing 36 containing the controller 38 and the processor 40. The controller 38 is configured for controlling the operational functions of the head-worn unit 22c, whereas the processor 40 is configured for processing the magnetic fields detected by the head-worn unit 22c to detect and localize the neural activity within the brain of the user 12. The auxiliary unit 24c may additionally include a power supply (which if head-worn, may take the form of a rechargeable or non-chargeable battery), a control panel with input/output functions, a display, and memory. Alternatively, power may be provided to the auxiliary unit 24c wirelessly (e.g., by induction).

The functionalities of the peripheral life/work context device 16, biofeedback device 18, and database, server, or cloud structure 20 may be the same as described above with respect to FIG. 1.

The peripheral life/work context device 16 is coupled to the auxiliary unit 24c of the brain interface assembly 14c (and/or the biofeedback device 18) via a wireless connection 42 (e.g., wireless radio frequency (RF) signals (e.g., Bluetooth, Wifi, cellular, etc.) or optical links (e.g., fiber optic or infrared (IR)) for communicating between the peripheral life/work context device 16 and the brain interface assembly 14c (and/or the biofeedback device 18). Alternatively, a wired connection between the peripheral life/work context device 16 and the brain interface assembly 14c (and/or the biofeedback device 18) may be used.

The biofeedback device 18 is coupled to the brain interface assembly 14c (and in this case, to the auxiliary unit 24c) via a wired connection 44 (e.g., electrical wires). Alternatively, a non-wired connection (e.g., wireless radio frequency (RF) signals (e.g., Bluetooth, Wifi, cellular, etc.) or optical links (e.g., fiber optic or infrared (IR)) for providing power to or communicating between the respective the auxiliary unit 24c of the brain interface assembly 14c and the biofeedback device 18 may be used.

The database, server, or cloud structure 20 may be coupled to the auxiliary unit 24b of the brain interface assembly 14c (and/or the peripheral life/work context device 16 and biofeedback device 18) via a wireless connection 46 (e.g., wireless radio frequency (RF) signals (e.g., Bluetooth, Wifi, cellular, etc.) or optical links (e.g., fiber optic or infrared (IR)) for providing power to or communicating between the biofeedback device 18 and the database, server or cloud structure 20. Alternatively, a wired connection between the database, server, or cloud structure 20 and the auxiliary unit 24c of the brain interface assembly 14c (and/or the peripheral life/work context device 16 and biofeedback device 18) may be used.

Figure 7A:
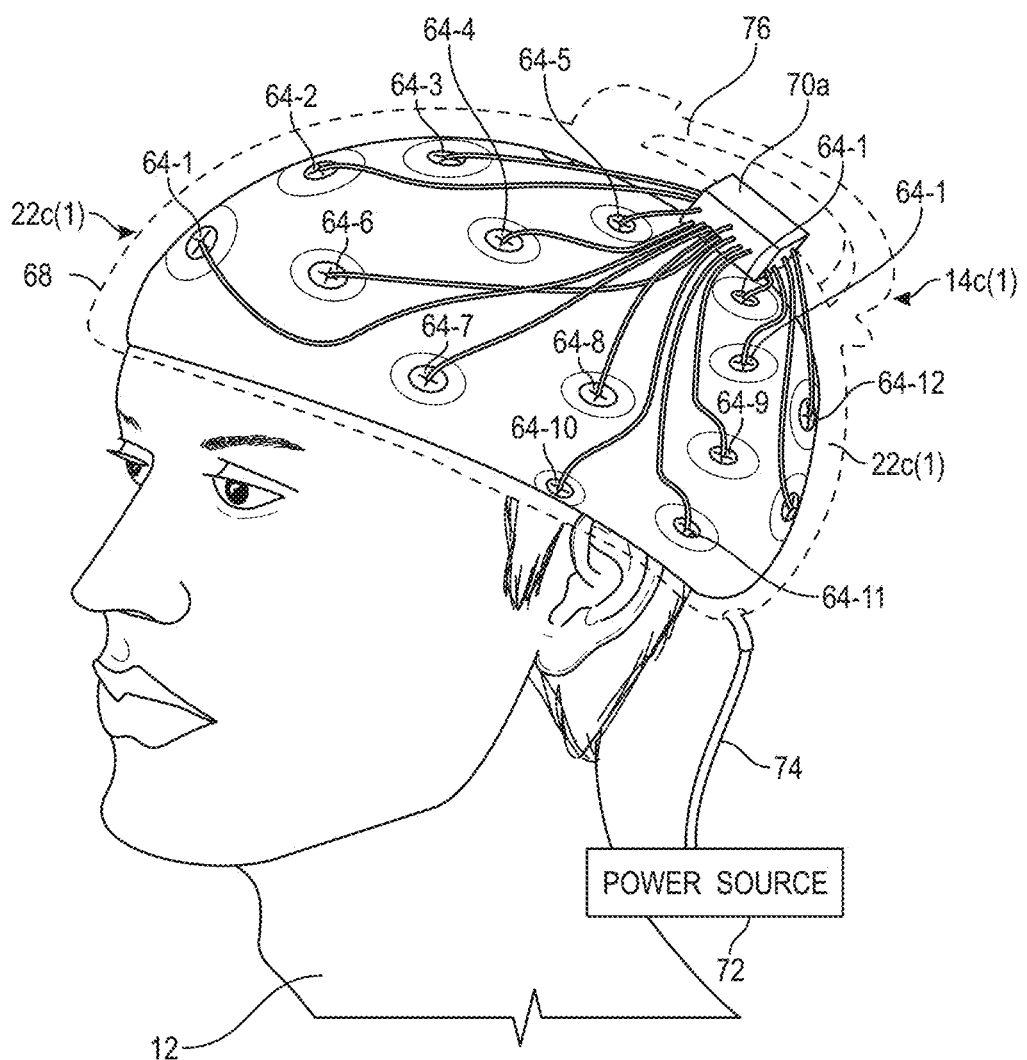
FIG. 7A-7C illustrate exemplary non-invasive wearable devices as used with the system of FIG. 6.
Figure 7B:
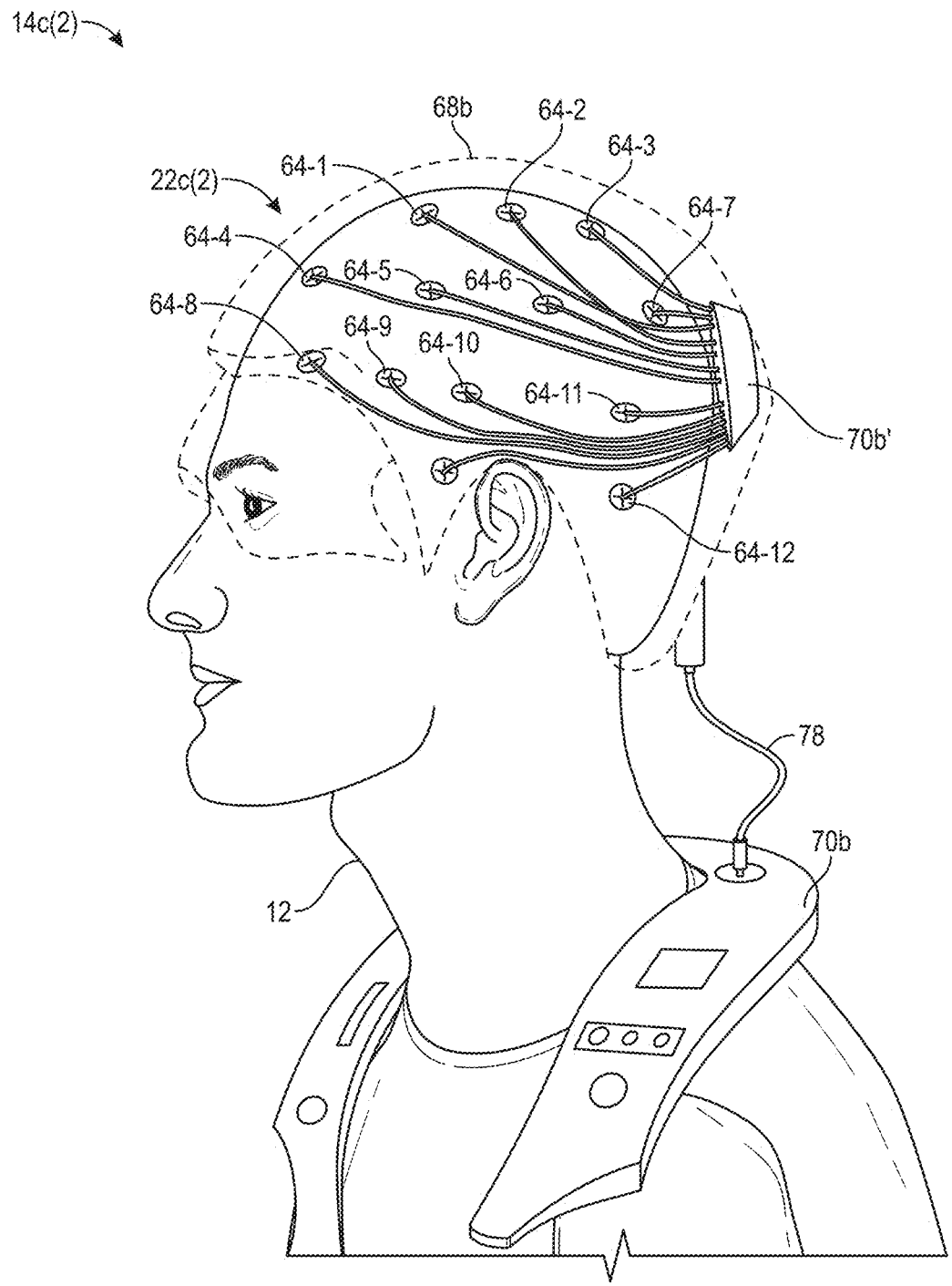
Figure 7C:
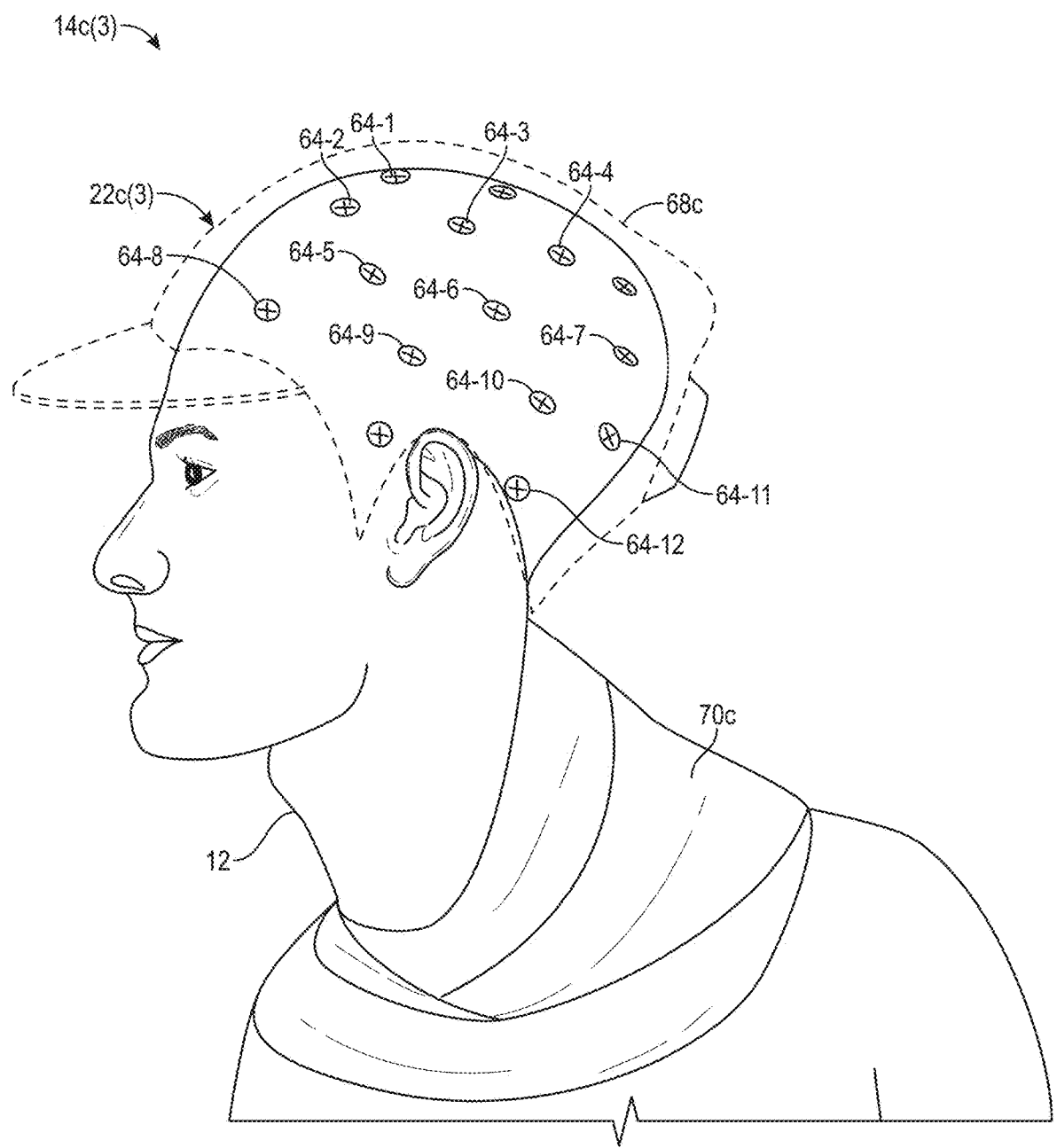

Referring now to FIGS. 7A-7C, different embodiments of the brain interface assembly 14c will be described. Such brain interface assemblies 14c may communicate wirelessly or via wire with the peripheral life/work context device 16, biofeedback device 18, and database, server, cloud structure 20, as described above. Each of the brain interface assemblies 14c described below comprises a head-worn unit 22c having a plurality of OPMs 64, a passive shield 66, and a support housing structure 68 in which the OPMs 64 and passive shield 66 are embedded. Each of brain interface assemblies 14c may also comprise a control/processing unit 70 for controlling the operational functions of the OPMs 64, and processing the magnetic fields detected by the OPMs 64 to detect and localize the neural activity within the brain of the user 12. As will be described in further detail below, the control/processing unit 70 may be contained in the head-worn unit 22c or may be incorporated into a self-contained auxiliary unit. As will be set forth below, the support housing structure 68 may be shaped, e.g., have a banana, headband, cap, helmet, beanie, other hat shape, or other shape adjustable and conformable to the user's head, such that the magnetometers 64 are in close contact with the outer skin of the head, and in this case, the scalp of the user 12.

As shown in FIG. 7A, a brain interface assembly 14c(1) comprises a head-worn unit 22c(1) and a power source 72 coupled to the head-worn unit 22c(1) via a wired connection 74. The head-worn unit 22c(1) includes the OPMs 64 (shown as 64-1 through 64-12) and a controller 70a. The head-worn unit 22c(1) further includes a support housing structure 68a that takes a form of a helmet that contains the OPMs 64, passive shield 66, and controller 70a. The material for the helmet 68a may be selected out of any suitable cloth, soft polymer, plastic, hard shell, and/or any other suitable material as may serve a particular implementation. The power source 72 may be implemented by a battery and/or any other type of power source configured to provide operating power to the magnetometers 64, controller 70a, and any other component included within the brain interface assembly 22c(1) via the wired connection 74. The head-worn unit 22c(1) optionally includes a handle 76 affixed to the helmet 68a for providing a convenient means of carrying the head-worn unit 22c(1).

As shown in FIG. 7B, a brain interface assembly 14c(2) comprises a head-worn unit 22c(2) and a controller 70b coupled to the head-worn unit 22b(2) via a wired connection 78. The head-worn unit 22c(2) includes the OPMs 64 (shown as 64-1 through 64-12), and a support housing structure 68b that takes a form of a helmet that contains the OPMs 64 and passive shield 66. The material for the helmet 68b may be selected out of any suitable cloth, soft polymer, plastic, hard shell, and/or any other suitable material as may serve a particular implementation. Unlike the controller 70a of the brain interface assembly 14c(1) illustrated in FIG. 7A, which is contained in the head-worn unit 22c(1), the controller 70b is self-contained, and may take the form of a garment (e.g., a vest, partial vest, or harness) for being worn on the shoulders of the user 12. The self-contained controller 70b may additionally include a power supply (which if head-worn, may take the form of a rechargeable or non-chargeable battery), a control panel with input/output functions, a display, and memory. Alternatively, power may be provided to the self-contained controller 70b wirelessly (e.g., by induction). The head-worn unit 22c(1) optionally includes a crest or other protrusion 80 formed in the helmet 68b for providing means of carrying a controller 70b'.

As shown in FIG. 7C, a brain interface assembly 14c(3) comprises a head-worn unit 22c(3) and a controller 70c. The head-worn unit 22c(3) includes the OPMs 64 (shown as 64-1 through 64-12), and a support housing structure 68c that takes a form of a baseball cap that contains the OPMs 64 and passive shield 66. The material for baseball cap 68c may be selected out of any suitable cloth, soft polymer, plastic, hard shell, and/or any other suitable material as may serve a particular implementation. The controller 70c is self-contained, and may take the form of a garment (e.g., scarf) for being worn around the neck of the user 12. The self-contained controller 70c may additionally include a power supply (which if head-worn, may take the form of a rechargeable or non-chargeable battery), a control panel with input/output functions, a display, and memory. Alternatively, power may be provided to the self-contained controller 70c wirelessly (e.g., by induction).

In any of the embodiments illustrated in FIGS. 7A-7C, the passive shield 66 may be replaced with an active shield, and the magnetometers, and in this case the OPMs 64, may have a dual arrangement that is operated in scalar/vector modes and spin exchange relaxation free (SERF) modes. While there are many types of OPMs, in general, magnetometers operate in two modalities: vector mode and scalar mode. In vector mode, the OPM can measure one, two, or all three vector components of the magnetic field; while in scalar mode, the OPM can measure the total magnitude of the magnetic field.

Vector mode magnetometers measure a specific component of the magnetic field, such as the radial and tangential components of magnetic fields with respect to the scalp of the human head. Vector mode OPMs often operate at zero-fields and may utilize a spin exchange relaxation free (SERF) mode to reach femto-Tesla sensitivities. A SERF mode OPM is one example of a vector mode OPM, but other vector mode OPMs can be used at higher magnetic fields. These SERF mode magnetometers can have high sensitivity, but in general, cannot function in the presence of magnetic fields higher than the linewidth of the magnetic resonance of atoms of about 10 nT, which is much smaller than the magnetic field strength generated by the Earth. As a result, conventional SERF mode magnetometers often operate inside magnetically shielded rooms that isolate the sensor from ambient magnetic fields including Earth's.

Magnetometers operating in the scalar mode can measure the total magnitude of the magnetic field. (Magnetometers in the vector mode can also be used for magnitude measurements). Scalar mode OPMs often have lower sensitivity than SERF mode OPMs. However, scalar mode OPMs can operate in unshielded environments up to and including the Earth field, which is about 50 μT. Furthermore, as the magnetic readings from scalar mode OPMs do not suffer from long-term drifts and bias they are frequently used to calibrate other magnetic sensors.

In optically pumped magnetometers (OPMs), which are based on the precession of atomic spins, another classification is based on the strength of the effective magnetic field experienced by the atoms in the gas cell, where two regimes are identified: zero-field mode and finite-field mode. Finite-field OPMs operate in a regime where the magnitude of the field experienced is much larger than the width of their magnetic resonance. Examples of finite-field OPMs include both scalar and vector mode magnetometers in driven, relaxation, and free-induction decay modalities.

Zero-field OPMs operate in an effective magnetic field whose strength is smaller, or comparable, to the linewidth of the magnetic resonance of the atoms. It will be understood that a zero-field OPM need not operate in strictly zero magnetic field, but rather in a relatively low magnetic field as described in the preceding sentence. Examples of zero-field magnetometers include OPMs operating in SERF mode in either DC or modulated schemes. Zero-field magnetometers typically measure one or two vector components of the field and are among the most sensitive magnetometers to date. However, as their operation requires a low magnetic field environment, they are usually deployed inside expensive, bulky, and sophisticated magnetically shielded rooms.

Figures 9A, 9B:
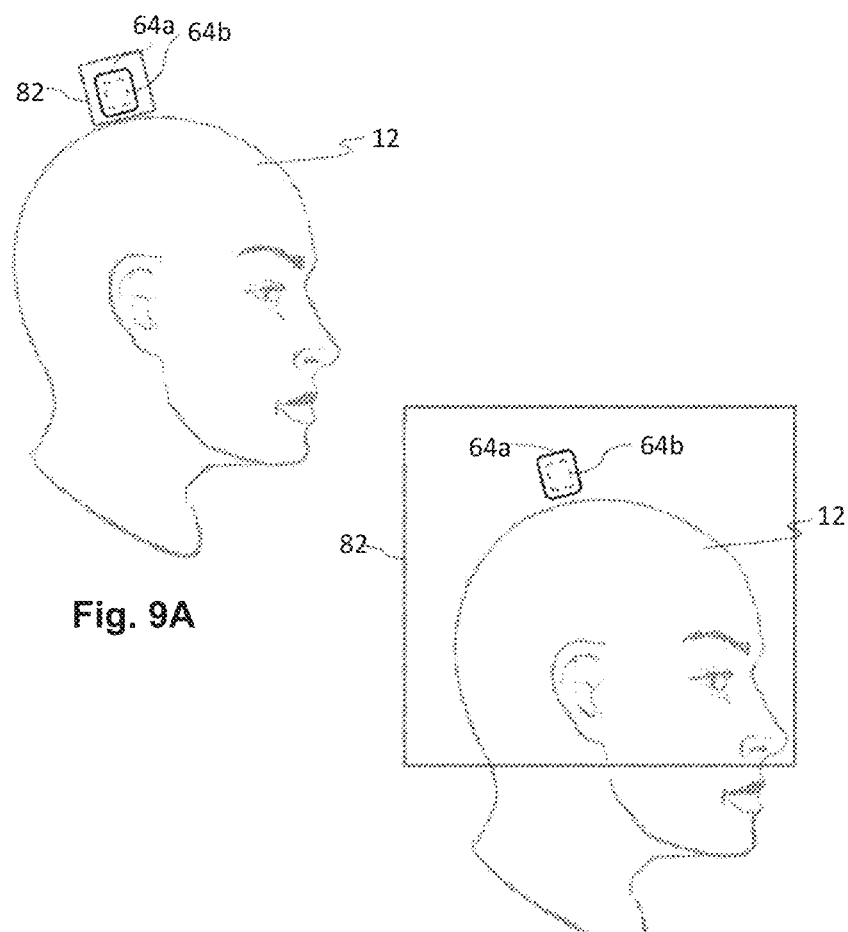
FIG. 9A is a schematic view of one embodiment of a dual arrangement of a SERF mode magnetometer and a scalar mode magnetometer in accordance with the present inventions.
FIG. 9B is a schematic view of another embodiment of a dual arrangement of a SERF mode magnetometer and a scalar mode magnetometer in accordance with the present inventions.

One dual-arrangement embodiment illustrated in FIG. 9A comprises a SERF mode magnetometer 64a and a scalar or non-SERF vector mode magnetometer 64b in combination with a magnetic field generator 82 that is placed on the scalp of the head of the user 12. In at least some embodiments, the magnetometers 64a, 64b are at the same location as the two magnetometers both use the same alkali vapor cell or the two magnetometers are actually the same magnetometer operating sequentially in i) the scalar or non-SERF vector mode and ii) the SERF mode. In other embodiments, the magnetometers 64a, 64b are separate from each other, but are preferably located close together.

Another embodiment of the dual arrangement illustrated in FIG. 9B comprises a SERF mode magnetometer 64a and a scalar or non-SERF vector mode magnetometer 64b in combination with a magnetic field generator 82 that is placed around a portion of the head of the user 12. The dual arrangement of the SERF mode magnetometer 64a and the scalar or non-SERF vector mode magnetometer 64b can include, but is not limited to, a) a single magnetometer that alternates operation in i) the SERF mode and ii) the scalar or non-SERF vector mode or b) an arrangement using a single vapor cell with a first portion of the vapor cell operating as a SERF mode magnetometer and a second portion of the vapor cell operating as a scalar or non-SERF vector mode magnetometer.

Figure 10:
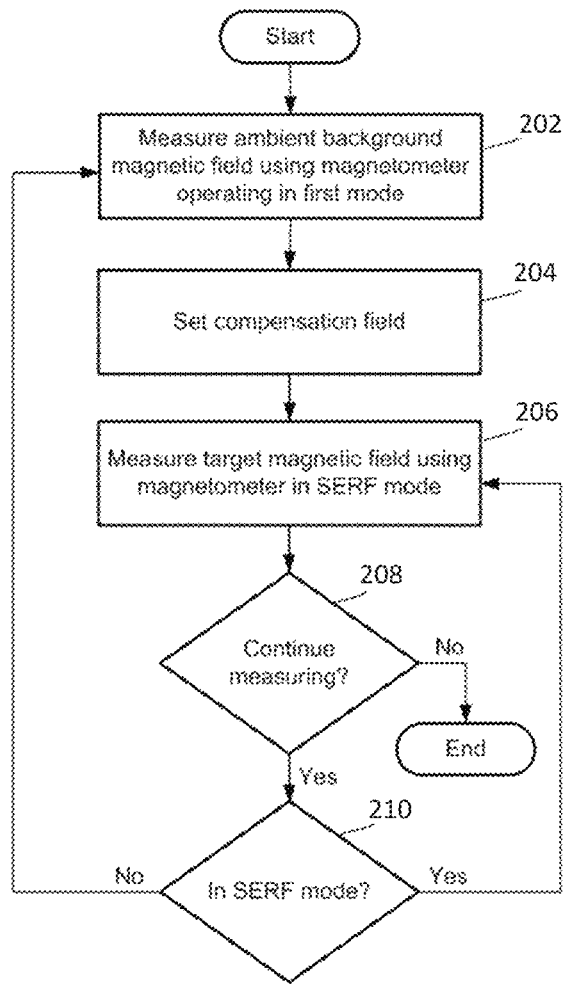
FIG. 10 is a flow diagram of one method of operating the dual arrangement of FIG. 9A or FIG. 9B.

FIG. 10 illustrates one embodiment of a method of operation or use of a dual arrangement of a SERF mode magnetometer 64a and a scalar or non-SERF vector mode magnetometer 64b, as well as active shielding using a magnetic field generator 82 or the like, as illustrated in FIGS. 9A and 9B. In step 202, the ambient background magnetic field is measured using the magnetometer operating in a first mode selected from a scalar mode or a non-SERF vector mode (i.e., the magnetometer 64b). The ambient background identifies the magnetic field or fields associated with sources other than magnetic field generator 82 and the biological source(s) (for example, neural signals from a user's brain) or other source(s) of interest. The ambient background magnetic field can include, for example, the Earth's magnetic field, as well as magnetic fields from magnets, electromagnets, electrical devices, and other signal or field generator in the environment, except for the magnetic field generator 82. In step 204, this ambient background field is canceled, or reduced substantially (e.g., by at least 80, 95, or 99 percent) by the application of a compensation field (i.e., a local field) using the magnetic field generator 82. The compensation field may be, for example, equal and opposite to the ambient background magnetic field or at least 80, 90, 95, or 99 percent of the ambient background magnetic field.

In step 206, the vector components of the magnetic field due to neural activity (or any other target magnetic field of interest) are measured using a magnetometer operating in a SERF mode different from the first mode (i.e., the magnetometer 64a). In step 208, it is determined whether to continue measuring. If no, then operation ends. If yes, then in step 210, it is determined whether the magnetometer 64a continues to operate in SERF mode. If yes, the method returns to step 206 to make another measurement. If no, such as when the compensation field is no longer sufficient to reduce the ambient background magnetic field to a magnitude that allows the magnetometer 64a to operate in SERF mode (for example, 200 nT, 50 nT, 20 nT, or less), then the method returns to step 202 to measure the ambient background magnetic field and, in step 204, modify or otherwise alter the compensation field.

As an alternative to step 210, the method may automatically switch from the SERF mode to the scalar or non-SERF vector mode periodically (for example, at a specific or selected repetition rate) or aperiodically to perform steps 202 and 204 again. In some embodiments, this switching between modes may occur at least every 0.5, 1, 2, 5, 10, 50, 100, or 500 milliseconds or every 0.5, 1, 2, 5, 10, or 30 seconds or every 1, 2, or 10 minutes.

Figure 11:
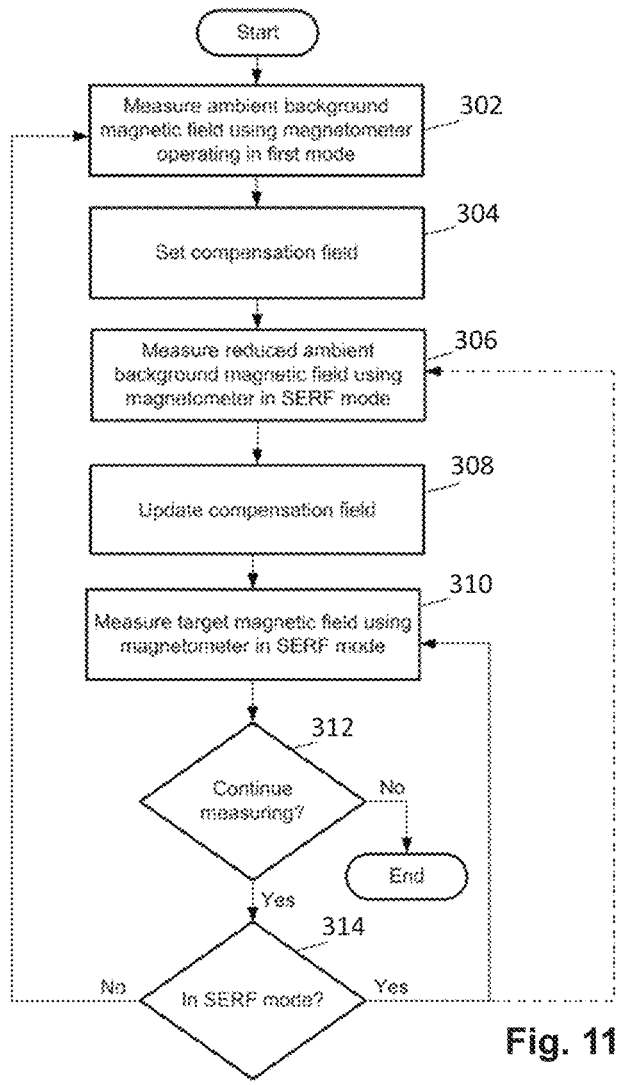
FIG. 11 is a flow diagram of another method of operating the dual arrangement of FIG. 9A or FIG. 9B.

FIG. 11 illustrates another embodiment of a method of operation or use of a dual arrangement of a SERF mode magnetometer 64a and a scalar or non-SERF vector mode magnetometer 64b, as well as active shielding using a magnetic field generator 82 or the like, as illustrated in FIGS. 9A and 9B. In step 302, the ambient background magnetic field is measured using the magnetometer operating in a first mode selected from a scalar mode or a non-SERF vector mode (i.e., the magnetometer 64b). In step 304, this ambient background field is canceled, or reduced substantially (e.g., by at least 80, 90, 95, or 99 percent) by the application of a compensation field (i.e., a local field) using the magnetic field generator 82. The compensation field may be, for example, equal and opposite to the ambient background magnetic field or at least 80, 90, 95, or 99 percent of the ambient background magnetic field. In step 306, a second measurement of the ambient background magnetic field (as reduced by the compensation field—i.e., the reduced ambient background magnetic field) is performed using a magnetometer operating in a SERF mode different from the first mode (i.e., the magnetometer 64a). In step 308, in response to this second measurement, the compensation field can be altered or updated to 'fine-tune' the cancelation or reduction of the ambient background magnetic field.

In step 310, the vector components of the magnetic field due to neural activity (or any other target magnetic field of interest) are measured using the magnetometer operating in the SERF mode (i.e., the magnetometer 64a). In step 312, it is determined whether to continue measuring. If no, then operation ends. If yes, then in step 314, it is determined whether the magnetometer 64a continues to operate in SERF mode. If yes, the method returns to step 310 to make another measurement or, optionally (indicated by the dotted line in FIG. 11), the method returns to step 306 to again measure the reduced ambient background magnetic field with the magnetometer in SERF mode to update the compensation field. If the magnetometer 64a is no longer operating in SERF mode in step 314, such as when the compensation field is no longer sufficient to reduce the ambient background magnetic field to a magnitude that allows the magnetometer to operate in SERF mode (for example, 200 nT, 50 nT, 20 nT, or less), then the method returns to step 302 to measure the ambient background magnetic field and, in step 504, modify or otherwise alter the compensation field.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A mental state awareness system, comprising:
   a non-invasive brain interface assembly configured for detecting brain activity of a user, the non-invasive brain interface assembly including:
      a head-worn unit configured for being worn on a head of the user;
      a plurality of magnetometers disposed in or on the head-worn unit and configured to detect magnetic fields, wherein a first one of the magnetometers is configured to operate in a first mode selected from a scalar mode and a vector mode, and a second one of the magnetometers is configured to operate in a spin exchange relaxation free (SERF) mode different from the first mode;
   at least one magnetic field generator; and
   a controller configured to control operational functions of the magnetometers, the controller further configured to:
      (i) measure an ambient background magnetic field using the first magnetometer in the first mode;
      (ii) generate, in response to the measurement of the ambient background magnetic field, a compensation field using the at least one magnetic field generator, wherein the compensation field reduces the ambient background magnetic field measured by the first magnetometer in the first mode;
      (iii) measure a target magnetic field using the second magnetometer in the SERF mode; and
      (iv) determine when the second magnetometer is not operating in the SERF mode and automatically performing steps (i) and (ii) again;
   a database, server, or cloud storage structure configured to track the measured target magnetic field as well as tracked magnetic field data of a pool of users;
   a processor configured to determine a mental state of the user, the determination based on a comparison of the tracked measured target magnetic field and the tracked magnetic field data of a pool of users; and
   a biofeedback device configured to automatically provide biofeedback to the user indicative of the determined mental state of the user.

2. The mental state awareness system of claim 1, wherein the mental state is one of anxiety, focus, attention, creativity, positive or negative reflections/attitude on experiences or the use of objects, and the employment of certain critical cognitive brain areas.

3. The mental state awareness system of claim 1, wherein the biofeedback device is configured to provide/direct vibrational signals to the user indicative of the determined mental state of the user through peripheral somatosensation.

4. The mental state awareness system of claim 3, wherein the vibrational signals are encoded with one or more messages.

5. The mental state awareness system of claim 1, wherein the biofeedback device is configured to provide/direct audio or visual signals to the user indicative of the determined mental state of the user.

6. The mental state awareness system of claim 1, further comprising a peripheral device configured to provide additional life/work context to the user.

7. The mental state awareness system of claim 6, wherein the peripheral device is configured to be programmed with one of a plurality of user experiences corresponding to the additional life/work context.

8. The mental state awareness system of claim 6, wherein the peripheral device is configured for automatically providing the additional life/work context to the user in response to the determined mental state of the user, such that the mental state of the user is modified.

9. The mental state awareness system of claim 1, wherein the processor is configured to track life/work context of the user, and acquire meta data in depth assessment of awareness and behavior modulation patterns of the user.

10. The mental state awareness system of claim 1, wherein each of the plurality of magnetometers comprises an optically pumped magnetometer.

11. The mental state awareness system of claim 1, wherein the controller is configured to reduce the measured ambient background magnetic field by the compensation field, and updates, in response to the measurement of the ambient background magnetic field reduced by the compensation field, the compensation field using the at least one magnetic field generator.

* * * * *